US008338420B1

(12) United States Patent
Kotera et al.

(10) Patent No.: US 8,338,420 B1
(45) Date of Patent: Dec. 25, 2012

(54) TREATMENT OF PARKINSON'S DISEASE AND ENHANCEMENT OF DOPAMINE SIGNAL USING PDE 10 INHIBITOR

(75) Inventors: Jun Kotera, Hasuda (JP); Takashi Sasaki, Kawaguchi (JP); Takeo Kitazawa, Ichikawa (JP); Taketoshi Ishii, Tokyo (JP); Hiroshi Morimoto, Amagasaki (JP); Harutami Yamada, Hasuda (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 12/647,880

(22) Filed: Dec. 28, 2009

Related U.S. Application Data

(63) Continuation of application No. 10/726,634, filed on Dec. 4, 2003, now abandoned.

(60) Provisional application No. 60/430,641, filed on Dec. 4, 2002, provisional application No. 60/430,642, filed on Dec. 4, 2002, provisional application No. 60/488,375, filed on Jul. 21, 2003.

(51) Int. Cl.
*A61K 31/50* (2006.01)
*A61K 31/40* (2006.01)
*C07D 471/22* (2006.01)

(52) U.S. Cl. ......... 514/247; 514/257; 514/365; 514/410

(58) Field of Classification Search .................. 514/247, 514/257, 365, 410
See application file for complete search history.

(56) References Cited

U.S. PATENT DOCUMENTS

| | | | |
|---|---|---|---|
| 3,961,060 A | 6/1976 | Fuxe | |
| 4,147,789 A | 4/1979 | Stutz et al. | |
| 5,017,607 A | 5/1991 | Chiesi | |
| 6,930,114 B2 | 8/2005 | Niewohner et al. | |
| 6,936,609 B2 | 8/2005 | Erguden et al. | |
| 2003/0008806 A1 | 1/2003 | Lebel et al. | |
| 2003/0078303 A1 | 4/2003 | Young et al. | |
| 2003/0229089 A1 | 12/2003 | Yamada et al. | |
| 2006/0106054 A1 | 5/2006 | Nagasawa et al. | |

FOREIGN PATENT DOCUMENTS

| | | |
|---|---|---|
| EP | 1 250 923 A2 | 10/2002 |
| EP | 1 281 771 A2 | 2/2003 |
| WO | WO-01/24781 A2 | 4/2001 |
| WO | WO-01/32170 A1 | 5/2001 |
| WO | WO-01/78711 A2 | 10/2001 |
| WO | WO-01/83460 A1 | 11/2001 |
| WO | WO-02/48144 A1 | 6/2002 |
| WO | WO-03/000269 A2 | 1/2003 |
| WO | WO-03/000693 A1 | 1/2003 |
| WO | WO-03/014115 A1 | 2/2003 |
| WO | WO-03/014116 A1 | 2/2003 |
| WO | WO-03/014117 A1 | 2/2003 |

OTHER PUBLICATIONS

Greengard, P. "The Neurobiology of Dopamine Signaling". Bioscience Reports, vol. 21, No. 3, Jun. 2001.*
Schmidt N. et al. "Neurochemical findings in the MPTP model of Parkinson's disease". J Neural Transm (2001) 108: 1263-1282.*
Yuasa et al., "Isolation and Characterization of Two Novel Phosphodiesterase PDE11A Variants Showing Unique Structure and Tissue-specific Expression", J. Bio. Chem., vol. 275, No. 40., 2000, pp. 31469-31479.
Sasaki et al., "Identification of Human PDE7B, a $_c$AMP-Specific Phosphodiesterase", Biochem. Biophys. Res. Commun., vol. 271, 2000, pp. 575-583.
Kotera et al., "Characterization and Effects of Methyl-2-(4-aminophenyl)-1,2-dihydro-1-oxo-7-(2-pyridinylmethoxy)-4-(3,4,5-trimethoxyphenyl)-3-isoquinoline Carboylate Sulfate (T-1032), a Novel Potent Inhibitor of $_c$GMP-Binding $_c$GMP-Specific Phosphodiesterase (PDE5)", Biochem. Pharmacol., vol. 60, 2000, pp. 1333-1341.
Fujishige et al., "Striatum- and testis-specific phosphodiesterase PDE10A isolation and characterization of a rat PDE10A", Eur. J. Biochem., vol. 266, 1999, pp. 1118-1127.
Waldeck et al., "Effect of Caffeine on Locomotor Activity and Central Catecholamine Mechanisms: a Study with Special Reference to Drug Interaction", Acta Pharmacol. Toxicol. Suppl. IV, vol. 36, 1975, pp. 1-23.
Fredholm et al., "Effect of Some Phosphodiesterase Inhibitors on Central Dopamine Mechanisms", Eur. J. Pharmacol., vol. 38, 1976, pp. 31-38.
Kakkar et al., "Inhibition of Bovine Brain Calmodulin-Dependent Cyclic Nucleotide Phosphodiesterase Isozymes by Deprenyl", Life Science, vol. 59, 1996, pp. PL 337-341.
Kakkar et al., "Amantadine: an antiparkinsonian agent inhibits bovine brain 60 kDa calmodulin-dependent cyclic nucleotide phosphodiesterase isozyme", Brain Research, vol. 749, 1997, pp. 290-294.
Hulley et al., "Inhibitors of Type IV Phosphodiesterases Reduce the Toxicity of MPTP in Substantia Nigra Neurons in Vivo", Eur. J. Neuroscience, vol. 7, 1995, pp. 2431-2440.
Dickie et al., "Chronic exposure to Ro20-1724 protects dopaminergic neurons in vitro against the neurotoxic action of N -methyl-D-aspartate and 1-methyl1-4-phenylpyridinium", Brain Research, vol. 753, 1997, pp. 335-339.
Hussain et al., "Treatment of erectile dysfuntion with sildenafil citrate (Viagra) in parkinsonism due to Parkinson's disease or multiple system atrophy with observations on orthostatic hypotension", J. Neurol. Neurosurg. Psychiatry, vol. 71, 2001, pp. 371-374.

(Continued)

*Primary Examiner* — Renee Claytor
(74) *Attorney, Agent, or Firm* — Birch, Stewart, Kolasch & Birch, LLP

(57) ABSTRACT

The present invention relates to a therapeutic or prophylactic method for treating Parkinson's disease by administering an effective amount of a compound having a phosphodiesterase 10 inhibitory activity; and also relates to a pharmaceutical composition for treatment or prophylaxis of Parkinson's disease comprising as an active ingredient a compound having a phosphodiesterase 10 inhibitory activity. Moreover, the present invention relates to a method for enhancing dopamine signal in the brain, which comprises administering an effective amount of a compound having a phosphodiesterase 10 inhibitory activity; and also relates to pharmaceutical composition for enhancing dopamine signal in brain comprising as an active ingredient a compound having a phosphodiesterase 10 inhibitory activity.

9 Claims, No Drawings

OTHER PUBLICATIONS

Swope et al., "Preliminary Report: Use of Sildenafil to Treat Dyskinesias in Patients with Parkinson's Disease", Neurology, vol. 54, 2000, A90-A91.

Fujishige et al., "Cloning and Characterization of a Novel Human Phosphodiesterase That Hydrolyzes Both cAMP and cGMP (PDE10A)", J. Bio. Chem., vol. 274, No. 26, 1999, pp. 18438-18445.

Kotera et al., "Characterization and Phosphorylation of PDE10A2, a Novel Alternative Splice Variant of Human Phosphodiesterase That Hydrolyzes cAMP and cGMP.", Biochem. Biophys. Res. Commun., vol. 261, 1999, pp. 551-557.

Sodering et al., "Isolation and characterization of a dual-substrate phosphodiesterase gene family: PDE10A", Proc. Natl. Acad. Sci. USA, vol. 96, 1999, pp. 7071-7076.

Loughney et al., "Isolation and characterization of PDA10A, a novel human 3', 5'-cyclic nucleotide phosphodiesterase", Gene, vol. 234, 1999, pp. 109-117.

Hebb et al., "Role of Phosphodiesterase in Neurological and Psychiatric Disease," 2007 Current Opinion in Pharmacology, vol. 7, pp. 86-92.

Giardina et al., "Adrogolide HCL (ABT-431, DAS-431), a Prodrug of the Dopamine D1 Receptor Agonist, A-86929," Preclinical Pharmacology and Clinical Data, 2001, CNS Drug Reviews, vol. 7, No. 3, pp. 305-316.

Schmidt et al., "Neurochemical Findings in the MPTP model of Parkinson's Disease," 2001, J. Neural Transm. vol. 108, pp. 1263-1282.

Greengard, "The Neurobiology of Dopamine Signaling," 2001, Bioscience Reports, vol. 21, No. 3, pp. 247-269.

Kehler et al., "The Potential Therapeutic Use of Phosphodiesterase 10 Inhibitors," 2007, Expert Opin. Ther. Patients, vol. 17, No. 2, pp. 147-158.

* cited by examiner

TREATMENT OF PARKINSON'S DISEASE AND ENHANCEMENT OF DOPAMINE SIGNAL USING PDE 10 INHIBITOR

This application is a Continuation of Ser. No. 10/726,634 filed Dec. 4, 2003, now abandoned, which application claimed the benefit of U.S. provisional application No. 60/430,641, filed Dec. 4, 2002, U.S. provisional application No. 60/430,642, filed Dec. 4, 2002, and U.S. provisional application No. 60/488,375, filed Jul. 21, 2003.

BACKGROUND OF THE INVENTION

1. Field of the Invention

The present invention relates to a novel method for treatment or prophylaxis of Parkinson's disease. The present invention also relates to a novel agent for treatment or prophylaxis of Parkinson's disease. Further, the present invention relates to a novel method for enhancing dopamine signals in the brain.

2. Prior Art

Parkinson's disease (also referred to as PD) is a progressive degenerate disorder of the central nervous system, characterized by symptoms such as tremor, rigidity, akinesia, postural reflex abnormalities (postural disturbance), etc.

With a partial exception of juvenile Parkinsonism, development of PD is frequently seen in 40's or 50's or later, and it is a disease of a high incidence, affecting one out of 2000 people (in the age of 65 or older, one out of 500 people).

Although neurons in the brain are lost and degenerated with aging even in a normal case, in a patient of the Parkinson's disease, significant loss and degeneration of neurons are observed in the substantia nigra of the midbrain, beyond a rate of normal aging. Therefore, it is thought that various kinds of symptoms of Parkinson's disease are caused due to decreasing of dopamine, which is one of the neurotransmitters produced in the substantia nigra of the midbrain.

Dopamine is involved in regulation of postural maintenance and speed of movement, and when an amount of dopamine produced is decreased, the symptoms of Parkinson's disease develops. It is known that dopamine decrease and development of symptoms have a close relationship. Further, when dopamine is decreased, a balance is lost between dopamine and acetylcholine, which is another neurotransmitter, leading to the symptoms of Parkinson's disease.

As stated above, Parkinson's disease is a representative disorder of the central nervous system, whose symptoms is expected to be alleviated by enhancement of dopamine signals in the brain, and as a therapeutic agent therefore, L-dopa, a dopamine precursor, etc. is employed.

Parkinson's disease and a treatment method thereof are summarized in review by Marsden et al. and Calne et al. (Marsden, Lancet, 1990, pp. 948-952; Calne, New England Journal of Medicine, 1993, vol. 329, pp. 1021-1027).

Among the therapeutic agents for Parkinson's disease, L-dopa is the most frequently used therapeutic agent. L-dopa is a precursor of dopamine, and L-dopa therapy is aimed to supplement dopamine, which is decreased in the substantia nigra-corpus striatum. Since dopamine does not cross the blood brain barrier (BBB), it will not reach the brain if it is administered into a circulating blood. However, L-dopa does cross the blood brain barrier (BBB), and it is metabolized by dopa decarboxylase in the brain to give dopamine, which in turn acts on a dopaminergic receptor.

However, along-termed administration of L-dopa causes complications such as dyskinesia, etc. Further, it has a problem of instability such as wearing-off phenomenon, on-off phenomenon, etc., or problem of showing unexpected reaction or involuntary movements.

Under such circumstances, there have been needs for developing a new excellent therapeutic agent for Parkinson's disease, or a new concomitant agent to avoid a high-dose administration of L-dopa.

Meanwhile, the following facts have been known, regarding a cyclic nucleotide phosphodiesterase of mammals. The cyclic nucleotide phosphodiesterase (hereinafter simply abbreviated as phosphodiesterase or PDE) is an enzyme that hydrolyzes a phosphodiester bond in a cyclic nucleotide such as cAMP (adenosine 3',5'-cyclic monophosphate) or cGMP (guanosine 3',5'-cyclic monophosphate), etc. as a substrate, to generate nucleotides such as 5'AMP (adenosine 5'-monophosphate) or 5'GMP (guanosine 5'-monophosphate), etc.

Cyclic nucleotides such as cAMP, cGMP, etc. are involved in regulations of many in vivo functions as the second messenger in the intracellular signal transduction. Intracellular concentrations of the cAMP and cGMP, changing in response to an extracellular signal, are regulated by a balance between an enzyme involved in a synthesis of cAMP and cGMP (adenylate cyclase and guanylate cyclase), and phosphodiesterase (PDE) involved in a hydrolysis thereof.

Until recently, many kinds of the phosphodiesterases have been isolated and identified in mammals, and they have been classified into plural types, according to homology of amino acid sequence, biochemical properties, characterization by an inhibitor, etc. (Beavo, Physiol. Rev., Vol. 75, pp. 725-748, 1995).

For example, PDE1 is $Ca^{2+}$/calmodulin dependent PDE and hydrolyses both cAMP and cGMP. PDE2 is activated by cGMP and hydrolyses both cAMP and cGMP. PDE classified as PDE3 is inhibited by cGMP. PDE4 specifically recognizes cAMP as a substrate, and is rolipram-sensitive. PDE5 specifically recognizes cGMP as a substrate. PDE6 is a photoreceptor cGMP-PDE. PDE7 specifically recognizes cAMP as a substrate, and is not sensitive to rolipram.

Further recently, existences of 4 kinds of novel types of PDE have been reported. PDE8 specifically recognizes cAMP as a substrate, and PDE9 specifically recognizes cGMP as a substrate. Both of PDE8 and PDE9 are reported to be insensitive to IBMX (3-isobutyl-1-methylxanthine), which is known to be a non-selective PDE inhibitor. Further, PDE11 recognizes both cAMP and cGMP as a substrate.

Regarding PDE10, the followings have been known. Although PDE10 (PDE10A) recognizes both cAMP and cGMP as a substrate, it has been reported to have a stronger affinity for cAMP. Further, cDNAs of human, mouse and rat PDE10A have been isolated and identified. Still further, existence of the PDE10 protein has been confirmed in rat (Fujishige et al., J. Biol. Chem., Vol. 274, pp. 18438-18445, 1999; Kotera et al., Biochem. Biophys. Res. Commun., Vol. 261, pp. 551-557, 1999; Soderling, et al., Proc. Natl. Acad. Sci. USA, vol. 96, pp. 7071-7076, 1999; Loughley, et al., Gene, vol. 234, pp. 109-117, 1999)

As a PDE10 inhibitor, the followings have been known. WO02/48144 (Bayer) discloses a pyrrolo[2,1-a]dihydro-isoquinoline compound having a PDE10 inhibitory activity. It is also described that these compounds with the PDE10 inhibitory activity show antiproliferative activity, and can be used as an anticancer agent. Further, it is also described they can be used for treatment of pains and/or for alleviating a fever in a state of having a fever. Further, in WO01/24781 (NovaNeuron), application of a modulator of PDE10 (PDE10A) for Huntington's disease is disclosed.

The followings have been known regarding a relationship between Parkinson's disease and the phosphodiesterase inhibitors. U.S. Pat. No. 4,147,789 (Sandoz) and U.S. Pat. No. 3,961,060 (Astra Lakemedal) disclose an application of non-specific PDE inhibitors such as caffeine, theophylline, etc., for treatment of Parkinson's disease, together with dopaminergic stimulants.

WO01/78711 (ICOS) discloses an application of a compound having an inhibitory activity on a cGMP specific PDE (PDE5) for treatment of Parkinson's disease.

WO01/32170 (Swope) discloses an application of PDE inhibitor such as sildenafil for a neurological symptom including Parkinson's disease, etc.

Hussain et al. discloses an application of sildenafil, which is PDE5 inhibitor and a medicament for erectile dysfunction for sexual dysfunction of patients of Parkinson's disease (Hussain et al., Journal of Neurology, Nuerosurgery and Psychiatry, 2001, vol. 71, pp. 371-374).

Swope et al. discloses an application of sildenafil for treatment of dyskinesia in Parkinson's disease (Swope, et al., Neurology, 2000, vol. 54, No. 7, pp. A90-A91).

In Dicki et al. and Hulley et al., it is described that a PDE4 inhibitor (Ro20-1724, etc.) is thought to show a protective activity on cells against neurotoxins (MPP+, MPTP, etc.) (Dicki et al., Brain Research, 1997, vol. 753, pp. 335-339; and Hulley et al., Eur. J. Neuroscience, 1995, vol. 7, pp. 2431-2440).

In Kakkar et al., it is described that deprenyl (MAO-B inhibitor) and amantadine, known therapeutic agents for Parkinson's disease are thought to show an inhibitory activity against a calmodulin dependent PDE (PDE1) (Kakkar et al., Brain Research, 1997, vol. 749, pp. 290-294; and Kakkar et al., Life Sciences, 1996, vol. 59, PL337-341).

Fredholm et al. describes that the activity of L-dopa is enhanced by application of PDE inhibitors (caffeine, IBMX, theophyllamine, dipyridamole, etc.) to an animal model (Fredholm et al., European Journal of pharmacology, 1976, vol. 38, pp. 31-38).

Waldeck reports that caffeine affects an activity of dopamine, and also suggests that this may be based on a PDE inhibitory activity that caffeine has (Waldeck, Acta Pharmacol. Toxicol. Suppl., 1975, vol. 36, pp. 1-23).

However, it has not been known, until today, to apply PDE10 inhibitor for treatment of Parkinson's disease.

Further, as regards to a dopaminergic receptor, the following facts have been known. It has been known that several kinds of dopaminergic receptors exist, and that dopamine type 1 receptor (D1-R) and dopamine type 2 receptor (D2-R) are mainly expressed in the brain.

It has been clearly known that Dopamine type 1 receptor (D1-R) conjugates with Gs (Gsα) of G protein and conjugates promotingly with an adenylate cyclase activity. On the other hand, although dopamine type 2 receptor (D2-R) is said to inhibitingly conjugate with adenylate cyclase, there is another theory, and certain points are remained unclear.

An object of the present invention is to provide a novel method for treatment or prophylaxis of Parkinson's disease. Another object is to provide a novel pharmaceutical composition for treatment or prophylaxis of Parkinson's disease. Still further object of the present invention is to provide a novel method or agent for enhancing dopamine signals in the brain in vivo. Objects other than those above are clear from the following descriptions.

SUMMARY OF THE INVENTION

The present inventors have found out that a compound having an inhibitory activity on phosphodiesterase 10 has an effect of enhancing an activity caused by L-dopa administration in Parkinson's disease model animals, that it can be used for alleviating the symptoms specific for Parkinson's disease, and that it enhances dopamine signals in the brain, whereby the present invention has completed.

The present invention relates to a therapeutic or prophylactic method for treating Parkinson's disease by administering to a patient an effective amount of a compound having a phosphodiesterase 10 inhibitory activity. Further the present invention relates to a pharmaceutical composition for treatment or prophylaxis of Parkinson's disease comprising as an active ingredient a compound having a phosphodiesterase 10 inhibitory activity. Still further, the present invention relates to a method for enhancing dopamine signals in the brain, which comprises administering to a patient an effective amount of a compound having a phosphodiesterase 10 inhibitory activity. Yet further, the present invention relates to a pharmaceutical composition for enhancing dopamine signals in the brain, specifically in vivo, comprising as an active ingredient a compound having a phosphodiesterase 10 inhibitory activity. Further, the present invention relates to the use of a compound having a phosphodiesterase 10 inhibitory activity for preparation of a medicament for treating Parkinson's disease, or for enhancing dopamine signals in vivo.

(Hereinafter, the compound having a phosphodiesterase 10 inhibitory activity is also referred to as "PDE10 inhibitor".)

It is thought that action mechanism for the pharmaceutical or the therapeutic method of the present invention is outlined as follows. Accordingly, the PDE10 inhibitor as an active ingredient acts on neurons expressing dopaminergic receptors in the brain, inhibiting an activity of PDE10, thereby suppressing decomposition of the second messenger, cAMP. It is thought that, through this action, signals caused by stimulation of the dopaminergic receptor (hereinafter referred to as dopamine signals) can be enhanced, and an effect of alleviating symptoms of Parkinson's disease is exhibited.

DESCRIPTION OF THE PREFERRED EMBODIMENT

Specific examples of the compound having a phosphodiesterase 10 inhibitory activity include pyrrolo[2,1-a]dihydroisoquinoline compounds included in the following formula:

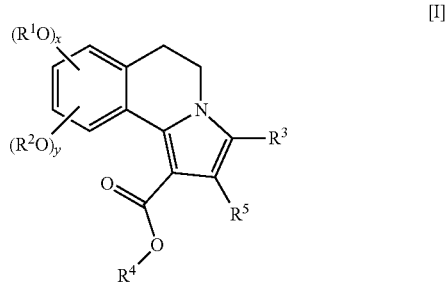

[I]

wherein
x and y independently from each other denote zero or 1 with the proviso that x+y=1 or 2;

$R^1$ and $R^2$ independently from each other denote hydrogen, $C_{1-4}$-alkyl or $CF_3$ or $R^1$ and $R^2$ together form a $C_{1-4}$-alkylene bridge;

$R^3$ and $R^4$ independently from each other denote $C_{1-4}$-alkyl;

$R^5$ denotes $C_{6-14}$-aryl, optionally having 1 to 3 further substituents selected from the group consisting of halogen;

$C_{1-6}$-alkyl which can be further substituted with one or more radicals selected from the group consisting of OH, halogen, $NH_2$ and $C_{1-6}$-alkoxy;

$C_{1-6}$-alkoxy which can be further substituted with one or more radicals selected from the group consisting of OH, halogen, $NH_2$, $C_{1-6}$-alkoxy, and $C_{6-10}$-aryloxy;

OH;

$NO_2$;

CN;

$CF_3$;

$OCF_3$;

$NR^6R^7$;

$SR^8$;

—O—$(CH_2)_{1-4}$—O— wherein the oxygen atoms are bound to the aryl moiety in ortho-position to each other; phenyloxy or benzyloxy wherein the phenyl moieties optionally contain one further substituent selected from the group consisting of $C_{1-6}$-alkyl, $C_{1-6}$-alkoxy, halogen and $NO_2$;

phenyl, optionally substituted with CN; and 4- to 9-membered aromatic heterocyclic ring containing 1 to 4 heteroatoms selected from the group consisting of N, O, and S;

$R^6$ and $R^7$ independently from each other denote hydrogen, $C_{1-6}$-alkyl, or together with the nitrogen atom to which they are attached, form a 5- to 7-membered saturated, partially unsaturated or aromatic ring which can contain up to 3 further hetero atoms selected from the group consisting of N, O, and S, and which ring can contain 1 to 3 substituents selected from the group consisting of $C_{1-6}$-alkyl, $C_{1-6}$-alkoxy, $C_{6-10}$-aryl and 4- to 9-membered aromatic heterocyclic ring containing 1 to 4 hetero atoms selected from the group consisting of N, O, and S; and $R^8$ denotes hydrogen, $C_{1-6}$-alkyl or $C_{6-10}$-aryl-$C_{1-6}$-alkyl;

with the proviso that 8,9-dimethoxy-3-methyl-2-phenyl-5,6-dihydro-pyrrolo[2,1-a]isoquinoline-1-carboxylic acid ethyl ester is excluded, and a pharmaceutically acceptable salt thereof, etc., specifically disclosed in WO02/48144 (incorporated herein by reference).

Other than the above, as the compound having a phosphodiesterase 10 inhibitory activity, there are mentioned, for example, Compound Y and Compound Z, which are pyrimidine derivatives represented by the following formulae, and pharmaceutically acceptable salts thereof. These compounds also have a PDE5 (PDEV) inhibitory activity, as well as a PDE10 inhibitory activity.

Compound Y and Compound Z and pharmaceutically acceptable salts thereof, and derivatives thereof can be prepared according to a method disclosed in WO01-83460 (incorporated herein by reference) (Examples 56 and 128), optionally in combination of conventionally known methods.

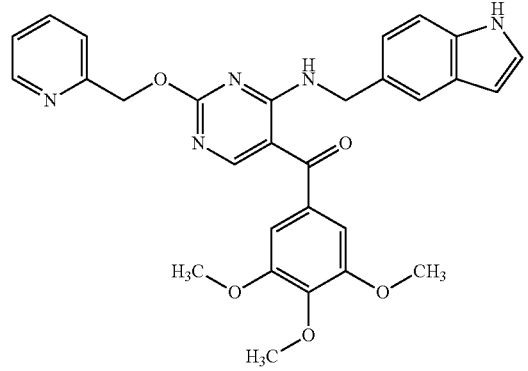

[Compound Y]

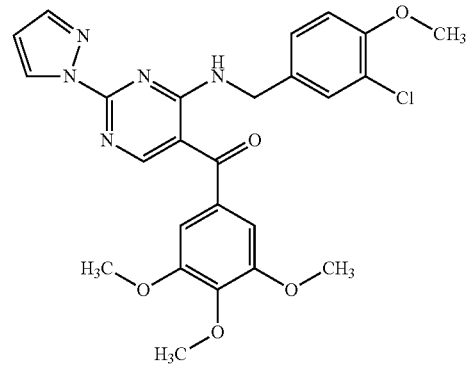

[Compound Z]

Besides the above, as the compounds having a PDE10 inhibitory activity, there are mentioned, for example, Compound A, a pyrimidine derivative represented by the following formula and pharmaceutically acceptable salt thereof. Compound A shows a strong inhibitory activity on PDE10, and it acts highly specifically on PDE10, showing 100 times or more as strong inhibitory activity on PDE10 ($IC_{50}$ value of 1/100 or less), as compared to inhibitory activities on other PDE families (for example, PDE1, 2, 3, 4, 5, 6, 7, 8, 9 and 11) Compound A and a pharmaceutically acceptable salt thereof can be prepared according to the below-described Preparation Examples, optionally in combination of the conventionally known methods.

[Compound A]

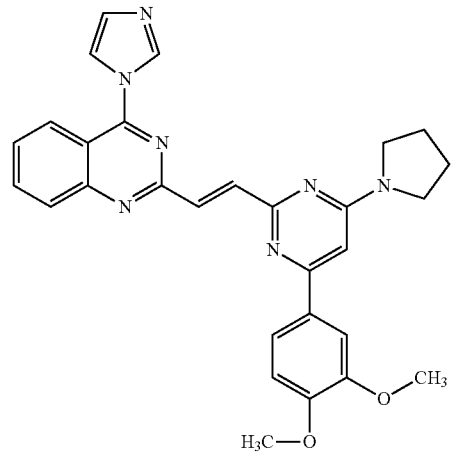

Compounds having a PDE10 inhibitory activity (hereinafter referred to as PDE10 inhibitors) are not limited to the above-mentioned specific examples. The compounds having a PDE10 inhibitory activity can be suitably selected and identified from natural compounds widely existing in the nature and newly synthesized compounds.

In the pharmaceutical composition and the therapeutic method of the present invention, PDE10 inhibitor to be used as an active ingredient is expected to have a strong inhibitory activity and affinity for PDE10, for the purpose of obtaining a stronger potency in terms of medicinal efficacy.

As such compounds, there may be mentioned, for example, a compound showing $IC_{50}$ value of normally 1 µM or less, preferably 300 nM or less, more preferably 100 nM or less, and particularly preferably 30 nM or less, and further preferably nM or less, when measured in the same manner as in the below-described Example 1, under the condition of substrate cAMP concentration of 0.25 µM.

Or, there are mentioned a compound having Ki value (inhibition constant) for PDE10 of normally 500 nM or less, preferably 150 nM or less, more preferably 50 nM or less, particularly preferably 15 nM or less, and further preferably nM or less. Further, in the pharmaceutical composition and the therapeutic method of the present invention, PDE10 inhibitor to be used as an active ingredient is expected to have a high selectivity for PDE10, for the purpose of minimizing side effects.

As such compound with high selectivity, there may be mentioned, for example, among the above-mentioned compounds having a strong inhibitory activity or affinity for PDE10, compounds having an inhibitory activity or affinity for PDE10 of normally 3 times or more, preferably 10 times or more, more preferably 30 times or more, and particularly preferably 100 times or more as high, as compared to inhibitory activities or affinities for PDE families other than PDE10 (ex., PDE 1, 3, 4, 5 and 6, etc. which are suggested to be involved in physiological activities).

For example, if $IC_{50}$ value (or Ki value) is taken as an index, the $IC_{50}$ value (or Ki value) as measured for PDE10 is normally 1/3 or less, preferably 1/10 or less, more preferably 1/30 or less, and particularly preferably 1/100 or less, as compared with the $IC_{50}$ value (or Ki value) as measured for the PDE families other than PDE10 (PDE 1, 3, 4, 5 and 6, etc.).

Selection and identification of the PDE10 inhibitors and measurements of inhibitory activities thereof can be carried out in the similar method as described below in Example 1 or conventionally known method as disclosed in literatures (for example, Fujishige et al., Eur. J. Biochem., vol. 266, pp. 1118-1127, 1999, etc.).

Further, selectivity of the PDE10 inhibitor may be evaluated, for example, by employing the similar method described in Example 2 below or the conventionally known method disclosed in the literatures (for example, Kotera et al., Biochem. Pharmacol., vol. 60, pp. 1333-1341, 2000; Sasaki et al., Biochem. Biophys. Res. Commun., vol. 271, pp. 575-583, 2000; Yuasa et al., Journal of Biological Chemistry, vol. 275, pp. 31469-31479, 2000, etc.), and comparing inhibitory activities (or affinities (Ki value)) as measured for PDE10 and for other PDE families. Through this method, it is possible to select and identify the compound having selective inhibitory activity for PDE10.

Still further, in the pharmaceutical composition and the therapeutic method of the present invention, PDE10 inhibitor exhibits its activity in the brain. Therefore, PDE10 inhibitor as an active ingredient is expected to have good brain uptake and penetration characteristics and show an intracerebral PDE10 binding kinetics which enables sustained inhibition of PDE10 in the brain.

Different from other tissue, the brain has the blood brain barrier (BBB) to restrict and regulate the movement of molecules between the blood and the brain. BBB consists of brain capillary endothelial cells. The brain capillary endothelial cells are connected through tight junction, and nutrients and drugs in the blood are required to pass transcellularly through the brain capillary endothelial cells. As a mechanism for the drugs to pass through the BBB, there are mentioned the following five routes; 1) passive diffusion, 2) carrier-mediated transport, 3) receptor-mediated transcytosis, 4) absorptive-mediated transcytosis and 5) active efflux transport by P-glycoprotein. The rate of the compound to pass through the BBB and enter the brain (PS) via one or plurals of these mechanisms can be measured by known in vivo experimental assays such as in situ brain perfusion, integration plot method, etc., or by the known in vitro experimental assays such as primary cultured brain capillary endothelial cells, or an established immortalized brain capillary endothelial cell line, etc. Further, intracerebral PDE10 binding kinetics of the compound can be confirmed by pharmacokinetics (PK) analysis and pharmacodynamics (PD) analysis.

In the present invention, PDE10 inhibitor to be used as an active ingredient may be in a free form, or when it can form a salt, it may be in a pharmaceutically acceptable salt. Examples of the pharmaceutically acceptable salt include an inorganic acid salt such as hydrochloride, sulfate, phosphate or hydrobromide, and an organic acid salt such as acetate, fumarate, oxalate, citrate, methanesulfonate, benzenesulfonate, tosylate or maleate, etc. In addition, in case that a compound has a substituent (s) such as carboxyl group, a salt with a base (for example, an alkali metal salt such as a sodium salt, a potassium salt, etc., or an alkaline-earth metal salt such as a calcium salt and the like) may be mentioned.

In the pharmaceutical composition or the therapeutic method of the present invention, administration route is not particularly limited, and generally employed oral or parenteral administration method (intravenous, intramuscular, subcutaneous, transdermal, transnasal, other transmucosal, enteral administration, etc.) can be applied.

Further, in case of using a compound which does not have good brain uptake and penetration characteristics, a method can be applied in which a pharmaceutical composition is directly or indirectly introduced into the brain, bypassing the BBB. Examples for the direct method include a method in which the compound is administered through catheter placed in the brain of a patient. More particularly, for example, there may be mentioned methods including intracerebroventricular (i.c.v.) administration, and a direct administration in corpus striatum. Such direct administration methods into the brain are in many case restricted in terms of invasiveness, when applied to treatment of human being, however, it is optionally be employed in evaluation for experimental animals, etc. As the indirect method, there are mentioned a method of converting a normally water-soluble drug into an fat-soluble drug or a prodrug (for example, by closing of hydroxyl, carbonyl, sulfate and primary amine groups, etc.), an administration method accompanying intravenous injection of hypertonic solution which enables temporary opening of the BBB (osmotic opening), etc.

In the pharmaceutical composition or the therapeutic method of the present invention, the active ingredient can be prepared into commonly used pharmaceutical preparations (a tablet, granule, capsule, powder, injection solution and inhalant, etc.), together with an inactive carrier, selected depending on an administration method. Examples of such carriers include a medical additive acceptable for general pharmaceuticals such as a diluent, binder, disintegrant, excipient and lubricant, etc.

In addition, in the pharmaceutical composition or the therapeutic method of the present invention, dose amount of the active ingredient may be optionally chosen, depending on potencies or properties of PDE10 inhibitors as an active ingredient, from a dose range which is effective enough for exhibiting a drug efficacy. The dose may vary depending on an administration route, age, bodyweight, and condition of a patient, and it is suitably selected from a generally used dose range, for example, a range of 0.01 to 300 mg/kg per day.

For example, when the PDE inhibitor as specifically disclosed in the above is used in a high-dose, there is a chance of lowering a movement of an individual, therefore, it is expected to select a suitable dose in consideration of such case.

The pharmaceutical composition or the therapeutic method of the present invention is applied for alleviating symptoms of Parkinson's disease.

For example, the therapeutic method may include the step of screening a patient of Parkinson's disease, and a step of administering to the patient an effective amount of a compound having a phosphodiesterase 10 inhibitory activity.

As symptoms of Parkinson's disease, for example, there are mentioned motor-related symptoms as follows:
Tremor;
Rigidity;
Akinesia or bradykinesia; and
Posture disturbances.
And relating to the above symptoms, there are observed
Gait disturbances; and
Speech impairment.

Further, in treatment of Parkinson's disease, L-dopa (a precursor of dopamine) is an important medicine to be used as a primary selected drug. However, as side effects accompanied by a long-termed use of this L-dopa, the patient often experiences dyskinesia. Dyskinesia is a functional disorder of voluntary movement (more specifically, a choreoid symptom which involuntary appears on face, neck, body, and limbs), and it becomes one of the big problems in treatment of Parkinson's disease. In addition to dyskinesia, wearing-off phenomenon, on-off phenomenon are also symptoms which are troublesome. In many cases, these symptoms can be alleviated by decreasing dose of L-dopa, however, decreased dose of L-dopa frequently is accompanied by worsening of Parkinsonian symptoms, which normally makes it difficult to deal with this problem.

The pharmaceutical composition or the therapeutic method of the present invention can enhance an effect of L-dopa to alleviate the Parkinsonian symptoms, by applying concomitantly with L-dopa to Parkinson's disease. Therefore, it is possible to decrease a dose of L-dopa or number of administration thereof, while maintaining an effect of L-dopa to alleviate the Parkinsonian symptoms, or it is possible to prolong a duration of an effect of L-dopa. Further, it can be expected to alleviate or delay development of unfavorable symptoms, accompanied by treatment using L-dopa, that is, dyskinesia, wearing-off phenomenon, on-off phenomenon, etc.

Further, it is expected that the pharmaceutical composition or the therapeutic treatment of the present invention is used in combination with L-dopa in a case where neuronal degeneration is advanced profoundly, however, in a case where neuronal degeneration is less advanced, it can be used singly to exhibit an effect.

The pharmaceutical composition or the therapeutic method of the present invention can be used in combination with L-dopa therapy, and it can also be used in combination with drugs for Parkinson's disease other than L-dopa. Examples of such drugs for Parkinson's disease other than L-dopa include:

Dopamine receptor agonists [bromocriptine, lisuride, pergolide, cabergoline, apomorphine, talipexole, ropinirole, pramipexole, SKF82958, SKF38393, Adrogolide (ABT-431; DAS-431), etc.];
MAO-B (type B monoamine oxidase) inhibitor [selegiline (deprenyl)];
COMT(catechol-O-methyl transferase) inhibitor [entacapone, tolcapone, etc.];
Dopa decarboxylase inhibitor for concomitant use with L-dopa [carbidopa, benserazide, etc.]
Dopamine release accelerator [amantadine, etc.];
Anticholinergic;
Adenosine receptor antagonist; and
NMDA antagonist, etc.

Among the above, in case of concomitant use of the dopamine receptor agonist and the pharmaceutical composition or the therapeutic method of the present invention, the activity of the dopamine receptor agonist can be enhanced based on the activity thereof.

Further, according to the present invention, the PDE10 inhibitor enhances dopamine signals in the brain. In other words, the method or the pharmaceutical composition of the present invention which uses PDE10 inhibitor can be applied to enhance dopamine signals in the brain in vivo, in living body, including in patients, by administering an effective amount of the inhibitor.

Corpus striatum (putamen and caudate nucleus), nucleus accumbens, olfactory tubercle and frontal lobe, etc. are known to be a part in which dopamine signals are involved.

On the other hand, PDE10 is confirmed to be expressed in corpus striatum (putamen and caudate nucleus), nucleus accumbens, olfactory tubercle, frontal lobe, temporal lobe, parietal lobe, occipital lobe, insular lobe, amygdala, dorsal lateral geniculate body (apart of thalamus), hippocampus, cerebellum, etc., in the brain of primates, and especially, strong expressions have been confirmed in corpus striatum (putamen and caudate nucleus), nucleus accumbens, and olfactory tubercle, etc. (Example 3 below). Further, in the brain of rodents, expression thereof has been confirmed in corpus striatum and nucleus accumbens and olfactory tubercle, etc.

Therefore, as a part of the brain in which dopamine signals can be enhanced by PDE10 inhibitor, there are mentioned corpus striatum (putamen and caudate nucleus), nucleus accumbens, olfactory tubercle, frontal lobe, etc. Particularly among them, preferable effect can be expected in corpus striatum (putamen and caudate nucleus), nucleus accumbens, olfactory tubercle, etc.

Further, as the intracerebral dopamine signals to be enhanced by PDE10 inhibitor, for example, there are mentioned dopamine signals induced by L-dopa administration, as well as intrinsic dopamine signals (i.e. dopamine signals based on endogenous dopamine) in vivo. In addition, dopamine signals induced by administration of dopamine receptor agonist are also mentioned.

Such dopamine signals include dopamine signals induced by administration of dopamine type 1 receptor agonist (D1 agonist), and also dopamine signals induced by administration of dopamine type 2 receptor agonist (D2 agonist).

Still further, dopamine signals induced by administration of dopamine type 1 receptor selective agonist (D1 selective agonist) or dopamine type 2 receptor selective agonist (D2 selective agonist) are included.

As described above, since the method or pharmaceutical composition of the present invention can enhance intracerebral dopamine signals in vivo, it is expected to exhibit a therapeutic or prophylactic effect for various central diseases, which are expected to be alleviated by enhancement of intracerebral dopamine signals.

As such central diseases, there are mentioned central diseases for which L-dopa or dopamine receptor agonist are applied for treatment or prophylaxis, specifically, for example, Parkinson's disease, Drug addiction, Cognitive impairment, Restless legs syndrome, and extrapiramidal syndrome accompanied by treatment of schizophrenia, etc.

As the dopamine receptor agonist, the same as the above are mentioned, among which, as the dopamine type 1 receptor agonist (D1 agonist), there are mentioned pergolide, cabergoline, apomorphine, SKF82958, SKF38393, Adrogolide (ABT-431; DAS-3), etc.

As the dopamine type 2 receptor agonist (D2 agonist), there are mentioned bromocriptine, lisuride, pergolide, cabergoline, apomorphine, talipexole, ropinirole, pramipexole, etc.

Among them, pergolide, cabergoline, apomorphine, etc. have activities as D1 agonist as well as D2 agonist.

On the other hand, SKF82958, SKF38393, Adrogolide (ABT-431; DAS-431), etc. are those having less or no activity as a D2 agonist, and are known to be an agonist selective for dopamine type 1 receptor (that is, a dopamine type 1 receptor selective agonist (D1 selective agonist)).

Further, bromocriptine, lisuride, talipexole, ropinirole, pramipexole, etc. are those having less or no activity as a D1 agonist, and are known to be a dopamine type 2 receptor selective agonist (D2 selective agonist).

In the present invention, L-dopa includes L-dopa itself and a prodrug (methyl ester, etc.) thereof, and a pharmaceutically acceptable salt thereof. Similarly, the dopamine receptor agonists include the dopamine receptor agonist itself and a prodrug thereof, and a pharmaceutically acceptable salt thereof.

Pharmaceutical effect for Parkinson's disease or an effect for enhancing dopamine signals in the brain of the pharmaceutical composition and therapeutic method of the present invention, or PDE10 inhibitor to be used therein as an active ingredient can be confirmed according to the known method or corresponding methods thereto.

For example, as a parkinsonian model animal, a mouse, a rat, a monkey or the like whose nigrostriatal neurons are impaired by using neurotoxins, etc. are used, and a pharmaceutical effect can be evaluated in vivo by administering drugs to these model animals.

Such models include, for example, an experimental animal such as a monkey, a marmoset, etc., which are treated by administering MPTP (1-methyl-4-phenyl-1,2,3,6-tetrahydropyridine) as a neurotoxin. In this model, dopaminergic neurons are degenerated by MPTP, and Parkinson-like symptoms such as motor disabilities are expressed, in which pharmaceutical effect can be evaluated by using alleviation of these symptoms as an index (Examples 6 and 7 below; Burns et al., Proc. Natl. Acad. Sci. USA, vol. 80, pp. 4546-4550, 1983; and Gerlach, et al., European Journal of Pharmacology, vol. 208. pp. 273-286, 1991, etc.).

Alternatively, there are mentioned experimental animals such as rats which are treated by administration of 6-hydroxydopamine (6-OHDA). 6-hydroxydopamine is a neurotoxin which mainly acts on catecholaminergic neurons, and has a dopamine depletion effect. In this model, by injecting 6-OHDA into the medial forebrain bundle of the test animal such as a rat, lesion can be formed in the nigrostriatal neurons on the administration side. Rotational behavior arise due to dopamine or dopamine agonist, and the pharmaceutical effect can be evaluated by taking the number of rotations as an index (Examples 5 and 8 below; and Koga et al., European Journal of Pharmacology, vol. 408, pp. 249-255, 2000, etc.).

Further, in addition to the above, as a simple method for evaluating pharmaceutical efficacy, there is mentioned a method in which an animal such as a mouse, a rat, etc. is treated by administration of reserpine. Reserpine inhibits transportation system of catecholamine including dopamine in the brain, causing depletion of dopamine in neurons. As a result, symptoms similar to those for Parkinson's disease, such as decrease in spontaneous movements are observed. The drugs are administered to the animal and the pharmaceutical effect can be evaluated by measuring the changes in spontaneous movements, etc. (Ferre et al., European Journal of Pharmacology, vol. 192, pp. 31-37, 1991).

Still further, for example, by using a method described in Example 4 below, or other known method, it is possible to confirm, in vitro, an enhancing effect for cAMP increase in the neurons stimulated by dopamine, etc., and to evaluate the strength of the enhancement.

The method and the pharmaceutical composition of the present invention are useful for treatment or prophylaxis of Parkinson's disease. Particularly, when it is used with L-dopa for enhancing the effect of L-dopa which is widely employed as a therapeutic agent of Parkinson's disease, it can decrease the dose amount or the number of administration of L-dopa and prolong a duration of an effect of L-dopa. In addition, it is expected to alleviate or delay development of unfavorable symptoms accompanied by L-dopa therapy.

Further, the method and the pharmaceutical composition of the present invention are useful for enhancing dopamine signals in the brain in vivo. Therefore, it is expected to show therapeutic or prophylactic effect for central diseases whose symptoms are expected to be alleviated by dopamine signal enhancement in the brain.

The pharmaceutical composition or the therapeutic method of the present invention exhibits its pharmaceutical efficacy (a therapeutic or prophylactic effect for Parkinson's disease, a dopamine signal enhancing effect in the brain, etc.), based on the PDE10 inhibitory activity possessed by the compound as an active ingredient.

Therefore, pharmaceuticals and therapeutic method expressing pharmaceutical efficacy, based on the activities other than this PDE10 inhibitory activity, are not included in the scope of the present invention.

For example, there has been a report on an application of non-specific PDE inhibitors (caffeine, IBMX, theophyllamine, dipyridamole, papaverine, theophylline, etc.), PDE5 inhibitor such as sildenafil, etc., or PDE4 inhibitor such as rolipram, etc. for animal models or for treatment of Parkinson's disease [Fredholm et al., European Journal of Pharmacology, 1976, vol. 38, pp. 31-38; Waldeck, Acta Pharmacol. Toxicol. Suppl., 1975, vol. 36, pp. 1-23; U.S. Pat. No. 4,147, 789; U.S. Pat. No. 3,961,060; WO01/78711; WO01/32170; Swope et al., Neurology, 2000, vol. 54, No. 7, pp. A90-A91; Dicki et al., Brain Research, 1997, vol. 753, pp. 335-339; and Hulley et al., Eur. J. Neuroscience, 1995, vol. 7, pp. 2431-2440]. However, effective applications to parkinsonian animal models or patients of Parkinson's disease, reported therein are not included in the present invention.

Hereinafter, the present invention will be explained in more detail by referring to the following Examples but these Examples do not intend to limit the present invention.

EXAMPLES

Example 1

Measurement of PDE10 Inhibitory Activity (1) Enzyme Preparation of PDE10 (PDE10A)

According to the methods described in Fujishige et al. (Fujishige et al., Eur. J. Biochem., vol. 266, pp. 1118-1127, 1999; and Mukai et al., Br. J. Pharmacol., vol. 111, pp. 389-390, 1994), the enzyme PDE10A was isolated and prepared as follows.

At first, corpus striatum was excised from bovine whole brain (Japanese Black Cattle, purchased from Tokyo Shibaura Zoki, co., Ltd.), and washed with ice-cold saline (0.9% sodium chloride). After the tissues were cut in a proper size, it was frozen by liquid nitrogen, and stored at −80° C.

To about 1.3 g of this tissue sample was added 8 ml of an ice-cold homogenization buffer I (20 mM Tris-HCl, pH 7.5, 2 mM magnesium acetate, 0.3 mM calcium chloride, 1 mM dithiothreitol, 1.3 mM benzamidine, 0.2 mM phenylmethylsulfonyl fluoride), and the resultant mixture was homogenized by Polytron homogenizer (PT10/35; available from KINEMATICA) for about 3 minutes. The homogenate was centrifuged by a low-speed centrifuge (M160-IV, rotor 50F-12A; available from Sakuma) at 8000 rpm, at 4° C. for 20 minutes, and the obtained supernatant was further centrifuged by an ultracentrifuge (Optima TLX Ultracentrifuge, rotor TLA100.4; available from Beckman) at 50000 rpm, at 4° C. for 60 minutes. The resultant supernatant was stored at 4° C.

Successively, this supernatant was applied to chromatography. Chromatography was performed using FPLC system (available from Amersham Biosciences). The above supernatant was applied to a HiTrapQ column (available from Amersham Biosciences) (5 ml bed volume) equilibrated by elution buffer (20 mM Tris-HCl, pH7.5, 1 mM calcium chloride, 1 mM dithiothreitol, 5 mM benzamidine). After washing the column with 20 ml of the elution buffer (flow rate, 2 ml/ml), and proteins were eluted from the column by running a sodium chloride gradient (0-400 mM 80 ml, followed by 400 mM-1000 mM 20 ml). Eluted fractions were collected by 2 ml each, and fractions eluted at a low salt concentration in the vicinity of the peak were mixed together.

To this fraction, glycerol was added to become 50%, and the mixture was stored at −20° C. This was used for an assay as PDE10 (PDE100A) enzyme solution.

Subsequently, as a result of analysis on enzymatic properties by carrying out the following PDE assay using this enzyme solution, it was confirmed that Km values for cAMP and cGMP were 0.17 µM and 3.9 µM, respectively, and almost corresponds to the Km values of PDE10 (human and rat) which have been reported. Further, as a result of studies on inhibitions by IBMX, zaprinast and dipyridamole, IC50 values were 9.2 µM, 13.7 µM and 1.3 µM, respectively, and it was confirmed that sensitivity for the inhibitors also corresponded to reported data.

(2) Measurement of a PDE10 Inhibitory Activity

The PDE assay was performed using the enzyme solution obtained in the above (1), and inhibitory activities of the compounds on PDE10 (PDE10A) were measured.

PDE assay was performed according to the method described in Kotera et al. (Kotera et al., Biochem. Pharmacol., vol. 60, pp. 1333-1341, 2000), by the radiolabeled nucleotide method as follows.

Accordingly, enzymatic reaction was carried out in 500 µl of the assay buffer containing as a substrate 4.8 nM [$^3$H]-cAMP and 0.25 µM unlabeled cAMP (available from Amersham Biosciences) [50 mM Tris-HCl, pH8.0, 5 mM MgCl$_2$, 4 mM 2-mercaptoethanol, 0.33 mg/ml bovine serum albumin].

After the reaction was carried out while keeping the temperature at 37° C. for 30 minutes, the reaction was stopped by boiling the reaction mixture for 2 minutes, and further added thereto was 100 µl of snake venom (Crotalus atrox snake venom 1 mg/ml) and the temperature was kept at 37° C. for 30 minutes. Subsequently, 500 µl of methanol was added thereto, and the reaction mixture was applied to Dowex column (1×8-400). Scintillation cocktail was added to each of the eluates, and the radioactivity was measured by scintillation counter. From them, PDE activity taking cAMP as a substrate (an activity to hydrolyze cAMP) was measured.

In the measurements of the inhibitory activities of compounds, a test compound was added to the above-mentioned reaction mixture, in various concentrations, and PDE activity was measured in the presence or absence of the test compound. From the measurements, PDE10 (PDE100A) inhibitory activities were obtained with respect to the various kinds of compounds.

IC$_{50}$ values were obtained, considering an outline by changing the concentrations of the inhibitor by order of 10, by calculating according to the linear equation method, using 2 inhibitory rates obtained from 2 different concentrations, taken from both sides nearest to 50% inhibition.

With respect to the compounds which shows the inhibitory activity, when the affinity to PDE is obtained as Ki values, it can be obtained, according to the conventional method, through detailed kinetic analysis of enzyme reactions. For example, PDE activities (initial reaction rates) are measured by performing an enzymatic reaction using a substrate (unlabeled AMP) in various concentrations and a test compound in various concentrations, and based on the measured values, Ki values are obtained by analysis such as the secondary plot of Lineweaver-Burk plot and Dixon plot, etc.

Alternatively, when the type of the inhibition is competitive inhibition, Ki values can be obtained based on the following formula, which represents the relation between Ki values and IC$_{50}$ values:

$$Ki=IC_{50}/(1+[S]/Km)$$

(Cheng-Prusoff equation) (Biochem Pharmacol, 22, 3099, 1973)

Example 2

Measurements of Inhibitory Activities for PDE Families Other than PDE 10

(1) Preparation of Enzymes of PDE Families Other than PDE10

According to the methods described in the literature, the enzyme of PDE families other than PDE10 were isolated and prepared as follows.

Enzyme preparations for PDE1, 2, 3, 4, 5 and 6 were done according to the method described in Kotera et al. (Biochem. Pharmacol., vol. 60, pp. 1333-1341, 2000).

Enzyme Preparation of PDE1

Ventricle was excised from SD rat anesthetized with sodium pentobarbital (Nihon SLC, about 300 g), and washed with 100 ml of ice-cold saline 3 times. After the tissues were cut in approximately 1 g, it was frozen by liquid nitrogen, and stored at −80° C.

To about 5 g of this tissue sample was added 16 ml of an ice-cold homogenization buffer I, and the resultant mixture was homogenized by Polytron homogenizer for 3 minutes. The homogenate was centrifuged at 8000 rpm, at 4° C. for 20 minutes, and the obtained supernatant was further centrifuged by an ultracentrifuge at 50000 rpm, at 4° C. for 60 minutes. The resultant supernatant was stored at 4° C.

Successively, this supernatant was applied to chromatography under the FPLC system, in the same manner as in Example 1 (1) above. Eluted fractions were collected by 2 ml each.

Subsequently, the eluted fractions were used as an enzyme solution for PDE assay. The reaction was performed in an assay buffer containing EGTA [ethylene glycol bis-(β-aminoethylether)-N,N,N',N' tetraacetic acid tetrasodium salt] (final concentration of 1 mM) or calcium chloride (final concentration of 2 mM) and calmodulin (40 unit s/ml), and cGMP-hydrolyzing activity was measured. As a result of PDE assay, the fraction was selected as a fraction containing PDE1, which showed higher activity in the presence of calcium chloride and calmodulin, as compared to the case in the presence of EGTA.

For these PDE1 containing fractions, cGMP hydrolyzing activities were analyzed in the presence of E4021 (100 nM), PDE5 specific inhibitor, it was shown that the cGMP-hydrolyzing activities in these fractions were not inhibited by E4021. From this fact, it was confirmed that these fractions were not contaminated by PDE5, which is eluted adjacent to PDE1.

Further, in the presence or absence of unlabeled cGMP, cAMP-PDE activities were measured for each of the fractions. PDE2 shows cGMP-hydrolyzing activity, and the presence of cGMP increases its cAMP hydrolyzing activity. The fractions showing such properties were excluded for the possibility of contamination of PDE2.

Still further, in the presence of rolipram (10 μm), the PDE4 specific inhibitor, cAMP hydrolyzing activities were measured for each of the fractions. The fractions showing clear inhibition by rolipram (10 μM) were excluded due to the possibility of contamination of PDE4.

The fractions satisfying the above conditions were selected and collected, and glycerol was added thereto to become 50%, and the mixture was kept at −20° C. This was used for PDE assay as PDE1 enzyme solution.

(1-2) Enzyme Preparation of PDE2

One adrenal gland of Japanese Black Cattle, purchased from Tokyo Shibaura Zoki, co., Ltd. was washed with 100 ml of ice-cold saline (0.9% sodium chloride) twice. Subsequently, the tissues were cut into about 1 gram, and it was frozen by liquid nitrogen. To about 2 g of this tissue sample was added 10 ml of an ice-cold homogenization buffer II (25 mM Tris-HCl, pH 7.5, 4 mM magnesium chloride, 0.5 mM EGTA, 2 mM dithiothreitol, 4 mM benzamidine, 0.1 mM phenylmethylsulfonyl fluoride), and the homogenate that was homogenized by Polytron homogenizer for 3 minutes was centrifuged at 8000 rpm, at 4° C. for 20 minutes, and the obtained supernatant was further centrifuged by an ultracentrifuge at 50000 rpm, at 4° C. for 60 minutes. The resultant supernatant was stored at 4° C.

This supernatant was applied to chromatography under the FPLC system, in the same manner as in Example 1 (1) above. Eluted fractions were collected by 2 ml each [provided that composition of the elution buffer and gradient of sodium chloride used were as follows:
Elution buffer composition: 25 mM Tris-HCl, pH 7.5, 0.1 mM EGTA, 1 mM dithiothreitol, 5 mM benzamidine
Gradient of sodium chloride: 0-500 mM 80 ml and 500 mM-1000 mM 20 ml].

Subsequently, the eluted fractions were used as an enzyme solution for PDE assay, and cGMP-hydrolyzing activity was measured. Or, cAMP-hydrolyzing activity was measured for respective fractions, in the presence or absence of unlabeled cGMP.

PDE2 shows an activity for hydrolyzing cGMP and cAMP, and the presence of cGMP increases its cAMP hydrolyzing activity. On the other hand, cAMP-hydrolyzing activity of PDE3 is inhibited by milrinone or cGMP. Further, PDE4 specifically hydrolyzes cAMP, and its cAMP-hydrolyzing activity is not affected by the presence of cGMP, and it is inhibited by rolipram, which is a PDE4 specific inhibitor. The cGMP-hydrolyzing activity of PDE5 is inhibited by 100 nM of E4021. The cGMP-hydrolyzing activity of PDE1 is increased by addition of 2 mM calcium chloride and 40 units/ml of calmodulin.

Using these properties as an index, the fractions containing PDE2 but not containing other PDE families were selected. These fractions were collected and glycerol was added thereto to become 50%, and the mixture was stored at −20° C. These were used as a PDE2 enzyme solution for PDE assay. The PDE activity of this enzyme solution was inhibited by EHNA [erythro-9-(2-hydroxy-3-nonyl)adenine], the PDE2 specific inhibitor, therefore, it was confirmed that this enzyme was PDE2.

(1-3) Enzyme Preparation of PDE3

Apex portion of ventricle of mixed-breed dog (Oriental Yeast) was excised, and washed with 500 ml of ice-cold saline three times. Subsequently, the tissues were cut into about 3 g, and it was frozen by liquid nitrogen, and stored at −80° C. To about 1 g of this tissue sample was added 10 ml of an ice-cold homogenization buffer II, and the resultant mixture was homogenized by Polytron homogenizer for 3 minutes. The homogenate was centrifuged at 8000 rpm, at 4° C. for 20 minutes, and the obtained supernatant was further centrifuged by an ultracentrifuge at 40000 rpm, at 4° C. for 60 minutes. The resultant supernatant was stored at 4° C.

This supernatant was applied to chromatography under the FPLC system, in the same manner as in Example 1 (1) above. Eluted fractions were collected by 2 ml each [provided that column, composition of the elution buffer and gradient of sodium chloride used were as follows:
Column: DEAE Sepharose FF column (20 ml bed volume, XK16/40 column; available from Amersham Biosciences)
Elution buffer composition: 25 mM Tris-HCl, pH 7.5, 0.1 mM EGTA, 1 mM dithiothreitol, 5 mM benzamidine
Gradient of sodium chloride: 0-600 mM 180 ml followed by 600 mM-1000 mM 40 ml].

Subsequently, the eluted fractions were used as an enzyme solution for PDE assay, and cGMP-hydrolyzing activity was measured. Further, cAMP-hydrolyzing activity was measured for respective fractions, in the presence or absence of unlabeled cGMP.

PDE3 shows an activity for hydrolyzing cGMP and cAMP, and the presence of cGMP inhibits its cAMP hydrolyzing activity. In the same manner as in (1-2) above, using the properties of PDE3 and other PDE families as indexes, the fractions containing PDE3 but not containing other PDE families were selected. These fractions were collected and glycerol was added thereto to become 50%, and the mixture was stored at −20° C. These were used as a PDE3 enzyme solution for PDE assay. The PDE activity of this enzyme solution was inhibited by milrinone, the PDE3 specific inhibitor, therefore, it was confirmed that this enzyme was PDE3.

(1-4) Enzyme Preparation of PDE4

The whole lung of mixed-breed dog (Oriental Yeast) was excised, and washed with 500 ml of ice-cold saline three times. Subsequently, the tissues were cut into about 3 g, and it was frozen by liquid nitrogen, and stored at −80° C.

To about 6 g of this tissue sample was added 15 ml of an ice-cold homogenization buffer, and the resultant mixture was homogenized by Polytron homogenizer for 3 minutes. The homogenate was centrifuged at 8000 rpm, at 4° C. for 20 minutes, and the obtained supernatant was further centrifuged by an ultracentrifuge at 50000 rpm, at 4° C. for 60 minutes. The resultant supernatant was stored at 4° C.

This supernatant was applied to chromatography under the FPLC system, in the same manner as in Example 1 (1) above. Eluted fractions were collected by 2 ml each [provided that column, and gradient of sodium chloride used were as follows:
Column: DEAE Sepharose FF column (20 ml bed volume, XK16/40 column; available from Amersham Biosciences)
Gradient of sodium chloride: 0-400 mM 180 ml followed by 400 mM-1000 mM 40 ml].

Subsequently, the eluted fractions were used as an enzyme solution for PDE assay, and cAMP-hydrolyzing activity was measured for respective fractions, in the presence or absence of unlabeled cGMP.

Activity of PDE4 is inhibited by rolipram, the PDE4 specific inhibitor. In the same manner as in (1-2) above, using the properties of PDE4 and other PDE families as indexes, the fractions containing PDE4 but not containing other PDE families were selected. These fractions were collected and glycerol was added thereto to become 50%, and the mixture was stored at −20° C. These were used as a PDE4 enzyme solution for PDE assay. The PDE activity of this enzyme solution was inhibited by rolipram, the PDE4 specific inhibitor, therefore, it was confirmed that this enzyme was PDE4.

(1-5) Enzyme Preparation of PDE5

In the same manner as in (1-4) above, the supernatant obtained from the homogenate of canine lung tissue was applied to chromatography under FLPC system, to collect eluted fractions of 2 ml each.

Subsequently, the eluted fractions were used as an enzyme solution for PDE assay, and cGMP-hydrolyzing activity was measured for respective fractions, in the presence or absence of E4021, the PDE5 specific inhibitor. The fractions which showed activity inhibition of 80% or more by E4021 were selected as fractions containing PDE5.

Further, for examining contamination of PDE1, which is adjacently eluted, cGMP-hydrolyzing PDE activity of the respective fractions were measured in the same assay buffer containing EGTA (final concentration of 1 mM) [or calcium chloride (final concentration of 2 mM) and calmodulin (40 units/ml)]. As a result of the assay, the fraction which showed higher activity in the presence of calcium chloride and calmodulin, as compared to that in the presence of EGTA were excluded, due to the possibility of contamination of PDE1.

These fractions were collected and glycerol was added thereto to become 50%, and the mixture was stored at −20° C. These were used as a PDE5 enzyme solution for PDE assay. The PDE activity of this enzyme solution was inhibited by sildenafil, the PDE5 specific inhibitor, therefore, it was confirmed that this enzyme was PDE5.

(1-6) Enzyme Preparation of PDE6

From the bovine eyeball, purchased from Tokyo Shibaura Zoki, co., Ltd., retina (pale red colored) which is present as a membrane on the pigmented layer was collected and stored at −70° C.

To buffer A [16 mM MOPS-NaOH, pH7.5, 1.6 mM dithiothreitol, 8 mM magnesium chloride, 96 mM potassium chloride, 48 mM sodium chloride, 0.16 mM phenylmethylsulfonyl fluoride, 10 μM pepstatin A, 10 μM leupeptin] (20 ml), sucrose (6 g) was dissolved. Added thereto was the above-mentioned retina (about 7 g), and the mixture was stirred for 30 minutes while cutting the retina by scissors. The mixture was applied to centrifugation at 2000 rpm, at 4° C. for 5 minutes and the supernatant was collected. To the resultant residue was added buffer B[10 mM MOPS, pH7.5, 1 mM dithiothreitol, 5 mM magnesium chloride, 60 mM potassium chloride, 30 mM sodium chloride, 0.1 mM phenylmethylsulfonyl fluoride, 10 μM pepstatin A, 10 μM leupeptin] (40 ml), and the mixture was stirred by rolling several times. This was applied to centrifugation and the resultant supernatant was combined with the above obtained supernatant. This is further centrifuged at 7000 rpm, at 4° C., for 5 minutes, and the precipitates were obtained as crude rod outer segment (ROS).

Subsequently, this was subjected to a stepwise sucrose density gradient centrifugation. Sucrose solutions with specific weights of 1.15, 1.13 and 1.11 (8 ml each) were layers from the bottom in this order, and a sucrose solution with specific weight of 1.10 (8 ml) in which the above crude ROS was suspended was layered on top of them, and they were subjected to an ultracentrifuge at 20000 rpm, 4° C. for 45 minutes. A red band appearing on the interface of the sucrose solution of specific weight of 1.11 and that with 1.13 were collected as ROS (rod outer segment).

This was diluted with 7 ml of buffer C [100 mM Tris-HCl, pH 7.5, 5 mM dithiothreitol, 5 mM magnesium sulfate, 0.1 mM phenylmethylsulfonyl fluoride, 10 μM pepstatin A, 10 μM leupeptin], and then, the mixture was subjected to an ultracentrifugation at 50000 rpm, at 4° C. for 20 minutes. The obtained precipitation was suspended in 2 ml of buffer C, and the suspension was left still on the ice and in room light for minutes. This was further subjected to an ultracentrifugation at 50000 rpm, at 4° C., for 20 minutes, and suspension-centrifugation process was repeated for the precipitation, several times, and then, to wash the precipitation. The obtained precipitation was suspended in 1.5 ml of buffer D [5 mM Tris-HCl, pH 7.5, 5 mM dithiothreitol, 0.5 mM magnesium sulfate, 0.1 mM phenylmethylsulfonyl fluoride, 10 μM pepstatin A, 10 μM leupeptin], and the suspension was centrifuged at 50000 rpm, at 4° C. for 20 minutes, to give a supernatant. For the precipitation, suspension and centrifugation were repeated for several times similarly, and the supernatant was combined with the above obtained supernatant and they were applied to a gel filtration.

Gel filtration was performed using SR25/45 column (available from Amersham Biosciences) packed with Bio-Gel A-1.5 m Gel, under FPLC system. To the column equilibrated with elution buffer [50 mM Tris-HCl, pH 7.5, 1 mM dithiothreitol, 150 mM sodium chloride] was applied a bovine serum albumin solution (1 mg/ml, 1 ml), and the column was washed with elution buffer. Subsequently, the above-obtained supernatant (about 2 ml) was applied to the column, and elution was performed by running elution buffer at a flow-rate of 0.5 ml/min for about 6 hours, to give eluted fractions of 3 ml each.

Further, PDE assay was carried out using the above-eluted fractions as an enzyme solution, and cGMP-hydrolyzing activity was measured. The fractions which showed a high cGMP-hydrolyzing activity was selected and mixed, and to the mixture were added bovine serum albumin (final concentration of 0.5 mg/ml), phenylmethylsulfonyl fluoride (0.1 μM), pepstatin A (1 μg/ml), leupeptin (1 μg/ml) and ethylene glycol (40%), and the mixture was stored at −20° C. Thus, light-activated PDE6 enzyme solution was obtained.

Subsequently, this light-activated PDE6 was activated by trypsinization. In other words, to the light-activated PDE6 enzyme (50-150 μl) were added a buffer solution [20 mM Tris-HCl (pH 7.5), 1 mM magnesium chloride, 0.5 mg/ml bovine serum albumin] to make the total volume 1 ml. Added thereto was a trypsin solution (7 mg/ml, 10 μl), and the mixture was left to stand at 4° C. for 30 minutes, and reaction was stopped by addition of a trypsin inhibitor solution (3 mg/ml, 100 μl). To the reaction mixture, ethylene glycol (0.7 ml) was added and the mixture was stored at −20° C. This was used for PDE assay as a trypsin-activated PDE6 enzyme solution.

(1-7) Enzyme Preparation of PDE9 (PDE9A)

Based on the information of cDNA sequence of human PDE9A (Genbank/EMBL Accession No. AF048837) (Fisher et al., J. Biol. Chem., 1998, vol. 273, pp. 15559-15564, 1999), a cDNA encoding human PDE9A was cloned by PCR method. Using this cDNA, a recombinant protein of human PDE9A was prepared as follows.

A DNA fragment comprising a cDNA encoding human PDE9A was linked to pFLAG-CMV-2 (available from Kodak), to give a vector plasmid for expression of human PDE9A, with a flag tag peptide added to the N-terminus. COS-7 cells were transfected by these vector plasmids, and the cells were cultured in Dulbecco's modified Eagle medium containing 10% bovine fetal serum for about 24 to 48 hours. After incubation, the cells were collected, and washed with Phosphate buffered saline, and re-suspended in a solution buffer (20 mM Tris-HCl, pH7.5, 2 mM magnesium acetate, 0.3 mM calcium chloride, 1 mM dithiothreitol, 1.3 mM benzamidine). The cells were homogenized by ultrasonic treatment, and subjected to centrifugation (100,000×g, 4° C., 1 hour) to collect a supernatant.

This supernatant containing the recombinant human PDE9A was used for PDE assay as a PDE9 (PDE9A) enzyme solution.

(1-8) Enzyme Preparations of PDE7 (PDE7A), PDE8 (PDE8A) and PDE 11 (PDE11A)

Based on the information of cDNA sequence of human PDE7A (Genbank/EMBL Accession No. NM002603), a cDNA encoding human PDE7A was cloned by PCR method, according to a method described in Sasaki et al. (Sasaki et al., Biochem. Biophys. Res. Commun., vol. 271, pp. 575-583, 2000). Further, based on the information of cDNA sequence of human PDE8A (Genbank/EMBL Accession No. AF388183), a cDNA encoding human PDE8A was cloned by PCR method, according to a method described in Gamanuma et al. (Gamanuma et al., Cell Signal, 2003, vol. 15, pp. 565-574). Further, a cDNA encoding human PDE11A was obtained, according to a method reported in Yuasa et al. (Yuasa et al., J. Biol. Chem., vol. 275, pp. 31469-31479, 2000). Using these cDNAs, recombinant proteins of human PDE7A, human PDE8A, and human PDE11A were prepared as follows.

DNA fragments comprising a cDNA encoding human PDE7A, human PDE8A or human PDE11A were linked to pcDNA4/HisMax (available from Invitrogen), to give a vector plasmid for expression of human proteins, with a histidine tag peptide (hexahistidine), added to the N-terminus. COS-7 cells were transfected with these vector plasmids, and the cells were cultured in Dulbecco's modified Eagle medium containing 10% bovine fetal serum for about 24 hours. The cultured cells were collected, and washed with phosphate buffered saline, and re-suspended in a solution buffer (40 mM Tris-HCl, pH7.5, 15 mM benzamidine, 5 μg/ml pepstatin A, 5 μg/ml leupeptin). The cells were homogenized by ultrasonic treatment, and subjected to centrifugation (100,000×g, 4° C., 1 hour) to collect a supernatant. Subsequently, a partial purification was performed by using a nickel affinity column. In other words, the above-obtained supernatant was applied to a nickel-nitrotriacetate resin (available from Qiagen) equilibrated with a solution buffer, and incubated by shaking at 4° C. for 3 hours. This resin was filled into a plastic column (0.8×5 cm), and the resins inside the column were washed with a washing buffer (40 mM Tris-HCl, pH7.5, 15 mM benzamidine, 200 mM sodium chloride, 5 mM imidazole, 5 μg/ml pepstatin A, 5 μg/ml leupeptin), and further, the proteins were eluted with an elution buffer (40 mM Tris-HCl, pH7.5, 15 mM benzamidine, 200 mM sodium chloride, 200 mM imidazole, 5 μg/ml pepstatin A, 5 μg/ml leupeptin), to collect fractions containing objective polypeptides. These were dialyzed with a solution buffer, and stored at −80° C.

The above-obtained solutions containing recombinant human PDE7A, recombinant human PDE8A, and recombinant human PDE11A were used for PDE assays as a PDE7 (PDE7A) enzyme solution, a PDE8 (PDE8A) enzyme solution, and a PDE11 (PDE11A) enzyme solution, respectively.

(2) Measurements of Inhibitory Activities on PDE Families

The PDE assays were performed using each of the enzyme solutions obtained in the above (1-1) to (1-8), in the same manner as in Example 1 (2) above, in the presence of test compounds in various concentrations or in the absence of the test compounds, provided that the substrates used in the PDE assays for each of the PDE families, were as follows:

PDE1: about 12 nM [$^3$H]-cGMP and 1 μM cGMP
PDE2: about 12 nM [$^3$H]-cGMP and 1 μM cGMP
PDE3: about 4.8 nM [$^3$H]-cAMP and 1 μM cAMP
PDE4: about 4.8 nM [$^3$H]-cAMP and 1 μM cAMP
PDE5: about 12 nM [$^3$H]-cGMP and 1 μM cGMP
PDE6: about 12 nM [$^3$H]-cGMP and 10 μM cGMP
PDE7 (PDE7A): about 4.8 nM [$^3$H]-cAMP and 0.1 μM cAMP
PDE8 (PDE8A): about 4.8 nM [$^3$H]-cAMP and 0.1 μM cAMP
PDE9 (PDE9A): about 12 nM [$^3$H]-cGMP and 0.1 μM cGMP
PDE10 (PDE100A): about 4.8 nM [$^3$H]-cAMP and 0.25 μM cAMP
PDE11 (PDE11A): about 12 nM [$^3$H]-cGMP and 1 μM cGMP According to the above, various compounds were assayed for inhibitory activities on each of the PDE families other than PDE10.

Example 3

Expression of PDE10 in the Brain (1) Expression of PDE10 (PDE10A) in the Human Brain (Detection by PDE Activities)

Respective parts of the human brain (frontal lobe, temporal lobe and nucleus accumbens) were examined with respect to the presence or absence of PDE10 (PDE100A) activities. PDE10 (PDE100A) activities in the respective parts of the brain were detected by measuring inhibitory activities using PDE10 (PDE10A) specific inhibitor, as follows.

As the PDE10 (PDE10A) specific inhibitor, a compound showing an excellent selectivity, exhibiting weak or no inhibitory activities towards PDE families other than PDE10 was used.

As a reference, to 14.8 mg of corpus striatum of rat brain was added 1 ml of a homogenation buffer (20 mM Tris-HCl, pH7.5, 2 mM magnesium acetate, 0.3 mM calcium chloride, 1 mM DTT, 1.3 mM benzamidine, 0.2 mM PMSF), and the mixture was homogenated by a sonicator, to give a homogenate. One μL of this homogenate was used as an enzyme solution, to perform PDE assays in the presence or absence of PDE10 (PDE100A) specific inhibitor.

Subsequently, 4 µL each of the homogenates of the human tissues (respective parts of human brain; frontal lobe, temporal lobe and nucleus accumbens) purchased from ABS Inc. were used to perform PDE assays in the presence or absence of the same PDE10 (PDE100A) specific inhibitor.

In the PDE assay, 0.25 µM cAMP was used as a substrate, and fractions which showed inhibition by PDE10 (PDE100A) specific inhibitor were taken as PDE10 (PDE100A) activity. Further, the PDE10 (PDE100A) specific inhibitor was used in a range of compound concentration of $1\times10^{-5}$ M to $1\times10^{-11}$ M, and an inhibition curve was obtained from the results of the assays.

Results:

According to the PDE 10 (PDE100A) assay using the homogenates of corpus striatum of rat brain as a reference, it was shown that based on the total PDE activities in the rat corpus striatum, about 80% thereof was PDE10 (PDE10A) activities. It can be expected that this is due to a crude condition in the tissues.

Subsequently, as results of the PDE 10 (PDE100A) assay using the homogenates of respective parts of the human brain (frontal lobe, temporal lobe and nucleus accumbens), PDE10 (PDE100A) activities were detected in any of the frontal lobe, temporal lobe and nucleus accumbens of the human brain. The ratio of PDE10 (PDE100A) activities to the total PDE activities was shown to be highest in nucleus accumbens, which was about 50% of the total PDE activities.

Expression of PDE10 (PDE10A) in marmoset brain (in situ hybridization) Localization of mRNA of PDE10A was studied by in situ hybridization method.

Probes for hybridization were prepared as follows. Using a plasmid pFLAG-H10A2 in which a cDNA encoding an entire coding region of human PDE10A2 was linked to pFLAG-CMV-2 (available from SIGMA), PCR was performed to give a cDNA fragment of human PDE10A (a fragment corresponding to nucleotides 1112-1449 of Gen-Bank accession number AB020593). Subsequently, this fragment was inserted into pGEM-Teasy (available from Promega), to prepare pGEM-h10A. This plasmid was cut with ApaI for sense probe, and with PstI for antisense probe, respectively, and DIG labeled by using DIG-labeling kit (available from Roche) to give sense probes and antisense probes.

In situ hybridization of the brain tissue was carried out as follows. After marmoset (3 years and 3 month old, male) was anesthetized with diethyl ether, the brain was excised, and Tissue-Tek optimal cutting temperature compound (Sakura Finetechnical Co., Ltd.) was dropped thereto. After the tissue was frozen on dry ice, 16 sections were cut out by a cryostat from the coronal section through brain and mounted on a polylysine slide glass. Each section was fixed with 4% formalin, treated with 10 µg/ml proteinase K for 7 minutes, and treated with 0.2 N HCl and 0.1 M triethanolamine/0.25% acetic anhydride. Subsequently, dehydration was performed by graded ethanols, prehybridization was done at 50° C. for 30 minutes by hybridization buffer, and hybridization was done using hybridization buffer containing probes, at 50° C. for 18 hours. After that, hybridization mixture was washed with high-stringent buffer at 60° C. for 30 minutes, and treated with RNaseA, and washed again with high-stringent buffer. Subsequently, signals were detected by DIG-detection kit (Roche).

Results:

As a result of the in situ hybridizations of the sections taken out from 16 points of the coronal section through brain, to cover the entire region of the marmoset brain, signals were observed, not only in corpus striatum, nucleus accumbens and olfactory tubercle, but also in frontal lobe, temporal lobe, parietal lobe, occipital lobe, insular lobe, amygdala, dorsal lateral geniculate body (a part of thalamus), hippocampus, cerebellum, etc. Signals were strongest in corpus striatum, nucleus accumbens and olfactory tubercle, and they were moderate in frontal lobe, temporal lobe, parietal lobe, occipital lobe, insular lobe, amygdala, dorsal lateral geniculate body (apart of thalamus), hippocampus and cerebellum.

Test of Coexpression of Dopamine Receptor and PDE10 (I) (in Situ Hybridization)

Expression patterns of a dopamine receptor (dopamine type 1 receptor) and PDE10 (PDE100A) in the marmoset brain was studied by in situ hybridization.

Probes for hybridization were prepared as follows. For preparation of probes of dopamine type 1 receptor, PCR was performed using human brain cDNA contained in Multiple Tissue cDNA Panels (Clontech) and a primer (5'-GC-CTTTGACATCATGTGCTC-3' and 5'-TAGATCCTGGTG-TAGGTGAC-3'), to give human D1 dopamine receptor fragment (Gen-Bank accession number NM000794, nucleotides 1011-1363). The fragment was inserted into pGEM-T easy (Promega), to prepare pGEM-hD1. The plasmid pGEM-hD1 was cut by SphI for sense probes, and cut by PstI for antisense probes. Further, the plasmid pGEM-h10A was cut by ApaI for sense probe, and cut by PstI for antisense probe. These were DIG labeled with DIG-labeling kit (Roche), to give sense probes and antisense probes.

In situ hybridization of the brain tissues were carried out as follows. Marmoset was systemically perfused with 100 ml of saline via heart, under etherization, and further perfused with 300 ml of a fixation solution, 4% paraformaldehyde-0.1M phosphate buffer in the similar manner, and the brain tissue was excised. The brain was immersed in the same fixation solution (4° C.) overnight, and sliced. The solution was replaced with 15%, 20% and 30% sucrose-0.1M phosphate buffers in this order, and embedded in optimal cutting temperature compound (OCT) (Tissue-Tek) in liquid nitrogen. After the frozen sections were prepared, in situ hybridizations for mRNAs of dopamine receptor (dopamine type 1 receptor) and PDE10 (PDE100A) were performed by using ISHR Starting Kit (NIPPON GENE).

Results:

The results of in situ hybridization were analyzed particularly paying close attention to the respective parts of corpus striatum, nucleus accumbens and frontal lobe. From the observations of any of the parts, it was clear that mRNAs of dopamine receptor (dopamine type 1 receptor) and PDE10 (PDE100A) were expressed in about 80% or more of the neurons. This means that most of the neurons coexpress both of the dopamine receptor (dopamine type 1 receptor) and PDE10 (PDE100A), and supports the fact that PDE10 (PDE10A) is involved in regulation of dopamine signals in the brain (corpus striatum, nucleus accumbens and frontal lobe).

Test of Coexpression of Dopamine Receptor and PDE10 (II) (in Situ Hybridization)

Coexpression patterns of dopamine receptor (dopamine type 1 receptor) and PDE10 (PDE100A) in marmoset brain was studied by double in situ hybridization technique.

Probes for hybridization were prepared as follows. The plasmid pGEM-h10A was cut by ApaI for sense probes and cut by PstI for antisense probes, to prepare sense and antisense probes with Fluorescein RNA Labeling Mix (Roche)

In situ hybridization of the brain tissue was performed as follows. Marmoset was systemically perfused with 100 ml of saline via heart, under etherization, and further perfused with 300 ml of a fixation solution, 4% paraformaldehyde-0.1M phosphate buffer in the similar manner, and the brain tissue was excised. The brain was immersed in the same fixation solution (4° C.) overnight, and sliced. The solution was replaced with 15%, 20% and 30% sucrose-0.1M phosphate buffers in this order, and embedded in optimal cutting temperature compound (OCT) (Tissue-Tek) in liquid nitrogen. After the frozen sections were prepared, double staining of in situ hybridization was performed by using ISHR Starting Kit (NIPPON GENE). Method and composition of the reagents were based on the protocol attached to the kit, and only the modified parts will be described. Proteinase treatment was carried out at a final concentration of 2 μg/ml for 15 minutes. Prehybridization and hybridization were done at 50° C. Probes were used by combining PDE10A-probes and D1 dopamine receptor-probes, and hybridization was done for 18 hours, with probe's concentration of 15 ng/ml each. Treatment with RNaseA was done for 30 minutes with a final concentration of 20 μg/ml. For signal detection, DIG nucleic acid detection kit and HNPP Fluorescent Detection Set (Roche) were used, and the method and composition of the reagents were based on the protocol attached to the kit. First, anti-DIG antibodies and HNPP/Fast Red TR, a fluorescent substrate were used to detect D1 receptors. The sections were blocked by 1% blocking buffer for 30 minutes, and then reacted for an hour with anti-DIG antibodies diluted for 500 folds with the blocking buffer. After washing, HNPP/Fast Red TR was reacted for 30 minutes, and signals were detected. Subsequently, each section was treated with 100 mM glycine-HCl (pH2.2) for 5 minute, twice, to dissociate anti-DIG antibodies, and subsequently PDE10A signals were detected. The sections were washed with PBS buffer, and blocked with 1% blocking buffer for 30 minutes, and were reacted for an hour with anti-FITC antibodies diluted for 100 folds with the blocking buffer. After washing, INT/BCIP was reacted in the dark for 18 hours, and PDE10A signals were detected. In order to confirm if the anti-DIG antibodies were dissociated, the blocking buffer not containing anti-FITC antibodies was used, and reaction with INT/BCIP was carried out, and the signals were not detected. Therefore, it was confirmed that signals colored by INT/BCIP were derived from PDE10A.

Results:

The results of in situ hybridization were analyzed particularly paying close attention to the respective parts of corpus striatum and frontal lobe. From the observations of any of the parts, it was clear that mRNAs of dopamine receptor (dopamine type-1 receptor) and PDE10 (PDE10A) were coexpressed in the same neurons. Further, it was shown that most of the neurons coexpress both of the dopamine receptor (dopamine type-1 receptor) and PDE10 (PDE10A), and this supports the fact that PDE10 (PDE100A) is involved in regulation of dopamine signals in the brain (corpus striatum and frontal lobe).

Example 4

Change in Intracellular cAMP in Neurons by PDE10 Inhibitor (1) Primary culture of neurons of corpus striatum Female Wistar rats on day 14 or day 15 of pregnancy were purchased from Japan SLC, Co. Ltd., and fetuses were taken out on day 18 of pregnancy. From the fetus, the brain was excised, and stored on ice-cold Leibovitz's L-15 medium (available from GIBCO) or on DMEM/F-12 medium (available from GIBCO). In the same medium, dura matter was removed and corpus striatum was collected. This striatum part was treated by trypsin to diffuse neurons, and the neurons were diluted and diffused in DMEM medium containing 10% bovine fetal serum. These neurons were inoculated in 48-well plate coated with 0.01% poly-L-lysine (available from Sigma) ($2 \times 10^5$ cells/well) and cultured. On the next day, the medium was changed to Neurobasal medium (available from GIBCO), containing 50 fold-diluted B-27 supplement (available from GIBCO), and then, half of the medium was replaced on day 4, 7 and 9 of culture, to continue culture.

(2) Measurement of Intracellular cAMP

As in the above (1), neurons were cultured, and on day 10 of culture, the medium was removed, and then, a test compound (PDE10 inhibitors, etc.) diluted with Hank's balanced salt solution were added, and incubated at 37° C. for 15 minutes. Following that, forskolin (final concentration of 1 μM) or dopamine (final concentration of 100 nM) or D1 agonist (SKF82958 Sigma) (final concentration of 3 nM, 10 nM, 30 nM) was added thereto, and further incubated at 37° C. for 15 minutes.

Intracellular cAMP was measured using cAMP EIA kit available from Amersham Biosciences. Accordingly, after removing the reaction mixture, lysis buffer 1B (attached to cAMP EIA kit) was added to stop the reaction, and to lead cytolysis, and intracellular cAMPs were extracted. An amount of cAMPs in the extract was measured according to a protocol attached to the cAMP EIA kit.

Various kinds of compounds having a PDE10 inhibitory activity were tested as in the above, and as a result of measurements of intracellular cAMP in the neurons, it was confirmed that the various compounds having PDE10 inhibitory activities enhanced intracellular cAMP increase caused by forskolin stimulus or dopamine stimulus or D1 agonist stimulus.

Example 5

Evaluation in Rat 6-hydroxydopamine Model (1)

Preparation of rat 6-hydroxydopamine model According to the method described in the literature (Koga et al., European Journal of Pharmacology, vol. 408, pp. 249-255, 2000), 6-hydroxydopamine (6-OHDA) was administered in the rat's brain, to cause lesion in the substantia nigra of the brain, to thereby cause motor disability. As the rats, male SD (Sprague Dawley) rats (about 9 to 10 week old) were used. To these rats was administered desipramine (available from Sigma) (25 mg/kg, i.p.). Desipramine was used after being dissolved in distilled water to be 25 mg/ml. After 15 minutes, pentobarbital (trade name: Nembutal Injection, available from Dainippon Pharmaceutical Co., Ltd.) was administered (50 mg/kg, i.p.) for anesthesia.

After it was confirmed that the rats were under anesthesia, hair was cut on the head, and median of scalp was incised for 3-4 cm long. Parietal bone was exposed and a hole was made on the bone by a hard metal cutter (Miniter Co., Ltd) in a diameter of about 1 mm, in the position of 2 mm to the right and 2.8 mm posterior to the bregma, to expose dura matter. The rat was placed in a brain stereotaxic frame, and according to the atlas of Watson et al. (Paxinos et al., 1986, "The Rat Brain in Stereotaxic Coordinates", Academic Press, New York), 4 μl of 6-OHDA (available from Sigma) (2 mg/ml) was administered into the medial forebrain bundle (2 mm to the right, 2.8 mm posterior and 8.5 mm ventral to the bregma), in a rate of 1 μl/minute using a microsyringe available from Hamilton. 6-OHDA was dissolved in ice-cold saline, in advance, to make the concentration 2 mg/ml, and the solution was frozen and kept at −20° C. under nitrogen gas. It was thawed on the day of experiment and cooled on ice until just before the administration.

After administration of 6-OHDA, the needle was maintained for 4 minutes in the same position, and it was removed from the brain and the scalp was sutured back.

One week after administration of 6-OHDA, apomorphine was administered, and rotational behaviors were confirmed to appear due to the lesion of substantia nigra by 6-OHDA in one hemisphere. Accordingly, after the rats were acclimated in 45 L cylindrical plastic bucket in 10 minutes or more, apomorphine (available from Sigma) was dorsally administered (0.1 mg/kg, s.c.), and the rats were returned to the plastic bucket, to measure rotational behaviors. Turnings were counted in every 5-minute interval, until rotational behaviors disappeared or until an event was repeated twice in which the number of turnings became 5 or less during the 5-minute interval. The rats showing total rotations of 90 or more were selected, and used for further experiments.

(2) Effects of Test Compounds on L-dopa Induced Rotational Behaviors

In the rat 6-OHDA model, the effects of test compounds on rotational behaviors induced by L-dopa administration was tested as follows.

To the model rat prepared in the above (1) (2 weeks after administration of apomorphine), L-dopa and benserazide (dopa decarboxylase inhibitor which inhibits degradation of L-dopa) were administered, and numbers of tunings were measured. Using the results as an index, grouping was performed, so that the total numbers of turnings were almost uniform among the groups.

To these rats, under light etherization, were administered test compounds (PDE10 inhibitors) or vehicle alone, and further administered were benserazide (2.5 mg/kg, i.p.) and L-dopa (10 mg/kg, i.p.), and turnings were counted in 5-minute intervals, as in the above (1).

L-dopa was administered 30 minutes after benserazide administration, and turnings were counted after L-dopa administration. A test compound (PDE10 inhibitor) (or vehicle alone) was intravenously administered 15 minutes before benserazide administration, under light etherization.

Benserazide (available from Sigma) was used after being dissolved in saline. L-dopa was used by dissolving a prodrug thereof, methyl L-DOPA (available from Sigma) in saline.

By comparing numbers of turnings of the group administered with the test compound (PDE10 inhibitor) and the group administered with vehicle alone, effects of the test compound (PDE10 inhibitor) to enhance or to prolong duration of rotational behaviors induced by L-dopa were evaluated.

Example 6

Evaluation in Marmoset MPTP Model (1)

Using marmoset MPTP models, effects of test compound on pharmaceutical efficacy of L-dopa administration were tested as follows.

About 16 weeks before carrying out the tests, marmosets were administered with MPTP (1-methyl-4-phenyl-1,2,3,6-tetrahydropyridine) (2.5 mg/kg, i.v.), according to the method described in the literature (Fukuzaki et al., Pharmacol. Biochem. Behav., vol. 67 No. 1, pp. 121-129, September 2000), to degenerate dopaminergic neurons in the brain, and individuals showing parkinsonian symptoms were used.

Using these marmosets (age 3-4 years, bodyweight 300-400 g), the following three kinds of tests were performed.

Each test was performed with respect to the same individual sequentially, and intervals of 5 days or more were allowed between the tests.

test 1: vehicle
test 2: vehicle and L-dopa+benserazide
test 3: test compound (PDE10 inhibitor) and L-dopa+benserazide 10 mg/kg of L-dopa and 2.5 mg/kg of benserazide (dopa decarboxylase inhibitor to inhibit degradation of L-dopa) were orally administered at the same time. Further, as test compounds, compounds confirmed with PDE10 inhibitory activities were administered via saphenous vein, 90 minutes (or 180 minutes) before administration of L-dopa+benserazide, under anesthesia by ketamine and isoflurane (In test 1 and test 2, only vehicle was administered in place of the test compound in the same manner).

L-dopa (available from Spectrum Chemical Mfg. Corp.) and Benserazide hydrochloride (available from Spectrum Chemical Mfg. Corp.) were suspended in 0.5% methylcellulose solution on the day of administration and used. A test compound (PDE10 inhibitor) was dissolved in a solvent 30 minutes before administration and used.

After administration of test compound (PDE10 inhibitor) (or vehicle) and L-dopa+benserazide, each individual was transferred to an activity cage equipped with four photo cell sensor units, and observation was continued for 6 hours at longest. For each individual, locomotor activity and motor disability score were evaluated in every 10-minute interval.

Motor disability was assessed according to the following 7 evaluation items, and total score of the 7 items were regarded as the motor disability score.

<Evaluation Item> (number in [ ] shows a score range, 0 means normal)

Alertness [0-2];
Checking movements [0-2];
Reaction to stimuli [0-3];
Attention and eye movements [0-1];
Posture [0-4];
Balance/coordination [0-3]; and
Vocalization [0-2]

Accordingly, for each of the individuals, results (changes in locomotor activity and motor disability score) of 3 kinds of tests were compared. By comparing the results of administration of L-dopa and vehicle alone (test 2) and the results of administration of L-dopa and the test compound (PDE10 inhibitor) (test 3), effects of the test compound (PDE10 inhibitor) for enhancing an activity of L-dopa or extending a sustained effect of L-dopa to alleviate the symptoms (that is, improvements in locomotor activity and motor disability score) were evaluated.

Example 7

Evaluation in Marmoset MPTP Model (2)

Bromocriptine (bromocriptine mesilate) is known to be a dopamine receptor agonist, and an agonist which acts on dopamine type-2 receptor (D2 agonist). As the dopamine type-2 receptor, subtypes of Dopamine 2, Dopamine 3 and Dopamine 4 exist, and bromocriptine acts agonistically on any type of them. On the contrary, as the dopamine type-1 receptor, subtypes of Dopamine 1 and Dopamine 5 exist, and bromocriptine is known to act antagonistically on Dopamine 1, and to act agonistically on Dopamine 5. (Japanese clinical medicine, vol. 58, No. 10, pp. 2066-2071).

Using bromocriptine (bromocriptine mesilate) as a dopamine receptor agonist, effect of test compound on pharmaceutical effects caused by administration of dopamine receptor agonist, in marmoset MPTP model was tested as follows.

The same method was employed as in Example 6, except for using bromocriptine (bromocriptine mesilate) in place of L-dopa and benserazide.

Each test was performed with respect to the same individual sequentially, and intervals of 5 days or more were allowed between the tests.

test 1: vehicle
test 2: vehicle and bromocriptine mesilate
test 3: test compound (PDE10 inhibitor) and bromocriptine mesilate 3 mg/kg of bromocriptine mesilate (available from Sigma) were orally administered. Further, as test compounds, compounds confirmed with PDE10 inhibitory activities were administered via saphenous vein, 90 minutes before administration of bromocriptine mesilate, under anesthesia by ketamine and isoflurane (In test 1 and test 2, only vehicle was administered in place of the test compound in the same manner).

Bromocriptine mesilate was suspended in 0.5% methylcellulose solution on the day of administration and used. Test compound (PDE10 inhibitor) was dissolved in a solvent 30 minutes before administration and used.

After administration of test compound (PDE10 inhibitor) (or vehicle) and bromocriptine mesilate, locomotor activity and motor disability score were evaluated for each individual, in the same manner as in Example 6.

Accordingly, for each of the individuals, results (changes in locomotor activity and motor disability score) of 3 kinds of tests were compared. By comparing the results of administration of bromocriptine mesilate and vehicle (test 2) and the results of administration of bromocriptine mesilate and the test compound (PDE10 inhibitor) (test 3), effects of the test compound (PDE10 inhibitor) for enhancing an activity of bromocriptine mesilate or extending a sustained effect of bromocriptine mesilate to alleviate the symptoms (that is, improvements of locomotor activity and motor disability score) were evaluated.

Example 8

Evaluation in Rat 6-Hydroxydopamine Model (2)

SKF38393 is known to be a dopamine receptor agonist which acts selectively on dopamine 1 receptors. Using SKF38393 as a dopamine receptor agonist, in rat 6-OHDA model, the effects of test compounds on rotational behaviors induced by administration of the dopamine receptor agonist was tested as follows.

Preparation of model rats and tests were performed in the same manner as in Example 5, except for using SKF38393 in place of L-dopa and benserazide.

However, rotational behaviors of the rats were measured by an 8-channel rat rotometer (available from Neuroscience Inc., Japan). Further, the rats were selected showing total rotations of 100 or more, induced by administration of apomorphine (0.1 mg/kg, s.c.). The rats were grouped, so that the numbers of turnings at apomorphine test were almost uniform among the groups, and used for the following tests.

To these rats, under light etherization, was administered a test compound (PDE10 inhibitor) (or vehicle alone), and further SKF38393 (0.02 mg/kg, s.c.) was administered, and numbers of turnings were counted (in every 5-minutes interval, over 150 minute).

SKF38393 (available from Sigma; S-168) was used after being dissolved in saline. The test compound (PDE10 inhibitor) (or vehicle alone) was administered intravenously from tail vein, under light etherization, 30 minutes before administration of SKF38393.

By comparing numbers of turnings of the group administered with the test compound (PDE10 inhibitor) and the reference group administered with a solvent alone, effects of the test compound (PDE10 inhibitor) to enhance or to prolong duration of rotational behaviors induced by dopamine receptor agonist were evaluated.

Example 9

Evaluation of Pharmacological Efficacy of PDE10 Inhibitor

With respect to Compound A obtained in the preparation example below, an inhibitory activity on PDE10 was examined in the same manner as in Example 1. Further, in the same manner as in Example 2, inhibitory activities on PDE families other than PDE10 were examined. Accordingly, $IC_{50}$ values were as shown in Table 1 below, and Compound A of the present invention was shown to have a specific inhibitory activity on PDE10. Further, from the estimated value from enzyme kinetic analysis, Ki value of Compound A of the present invention for PDE10 (PDE100A) was approximately 0.9 nM.

TABLE 1

| PDE Family | $IC_{50}$ (nM) |
|---|---|
| PDE10 (PDE10A) | 1.1 |
| PDE1 | >1000 |
| PDE2 | >1000 |
| PDE3 | >1000 |
| PDE4 | 160 |
| PDE5 | >1000 |
| PDE6 | 290 |
| PDE7 (PDE7A) | >1000 |
| PDE8 (PDE8A) | >1000 |
| PDE9 (PDE9A) | >1000 |
| PDE11 (PDE11A) | >1000 |

Further, with respect to Compound A of the present invention, change in intracellular cAMP in neuron was examined in the same manner as in Example 4. Accordingly, it was confirmed that Compound A (concentration 10 μM, 1 μM) enhanced intracellular cAMP increase caused by forskolin stimulus in neuron. It was also confirmed that Compound A (concentration 1 μM) enhanced intracellular cAMP increase caused by dopamine stimulus in neuron. Further, it was confirmed that Compound A (concentration 10 μM, 1 μM) enhanced intracellular cAMP increase caused by D1 agonist (SKF82958, available from Sigma) stimulus in neuron.

Further, Compound A (1 mg/kg, i.v.) was intravenously administered to rat, and according to integration plot method, a rate (PS) was measured for Compound A to enter the brain by passing through the blood brain barrier (BBB), and occupancy of PDE10 binding in the brain was analyzed. It was shown that Compound A had good brain uptake and penetration characteristics and an excellent PDE10 binding behaviors inside the brain.

Still further, in the same manner as in Example 5, effects of Compound A in the rat 6-hydroxydopamine model were examined. Accordingly, by administration of Compound A (1 mg/kg, i.v.), it was confirmed that rotational behaviors induced by L-dopa tended to increase in terms of total number of turnings, and Compound A significantly prolonged a duration of rotational behaviors. As stated above, Compound A enhanced L-dopa induced rotational behaviors in rat 6-hydroxydopamine model.

In the same manner as in Example 6, effects of Compound A were examined in marmoset MPTP model. By comparing the case in which Compound A (0.3 mg/kg or 1 mg/kg, i.v.) was administered together with L-dopa and the case in which vehicle alone was administered with L-dopa, it was shown that Compound A enhanced and/or prolonged duration of effects of L-dopa to alleviate symptoms (improvements of locomotor activity and motor disability score).

In the same manner as in Example 7, effects of Compound A were examined in marmoset MPTP model. By comparing the case in which Compound A was administered together with bromocriptine, a dopamine receptor agonist (D2 agonist) (0.3 mg/kg) and the case in which vehicle alone was administered with bromocriptine, it was shown that Compound A had a tendency to enhance the effects of bromocriptine to alleviate symptoms (improvements of locomotor activity and motor disability score).

In the above-stated tests using rat and marmoset model animals, Compound A which was prepared according to preparation example below was dissolved in a solvent (0.1N—HCl) just before administration, in accordance with the dose to be used in the experiments.]

From these results, Compound A was thought to enhance dopamine signals in the brain (corpus striatum, etc.), thereby exhibit a therapeutic effect on Parkinson's disease, based on its specific inhibitory action on PDE10.

Further, these results support the fact that compounds having a specific inhibitory activity on PDE10 enhance dopamine signals in the brain (corpus striatum, etc.) induced by administration of L-dopa or dopamine receptor agonist (D2 agonist such as bromocriptine, etc. and D1 agonist such as SKF82958, SKF38393, etc.), and the fact that they enhance the pharmaceutical effect of L-dopa or dopamine receptor agonists (effect to alleviate symptoms in Parkinson's disease, etc.).

Preparation Example Preparation of Compound A

Compound A, that is, 2-{(E)-2-[4-(1-imidazolyl)-quinazolin-2-yl]}ethenyl-4-(3,4-dimethoxy)phenyl-6-(pyrrolidin-1-yl)pyrimidine was prepared, according to the method described in the following (1) to (5).

(1) Synthesis of 2,4-dichloro-6-(3,4-dimethoxy)phenylpyrimidine 2,4,6-trichloropyrimidine (13.3 g), 3,4-dimethoxyphenylborate (13.2 g), and dichlorobis(triphenylphosphine)palladium(II) (2.50 g) were added to 1,2-dimethoxyethane (130 mL)-2M sodium carbonate aqueous solution (90 mL), and the mixture was stirred at 90° C. for 100 minutes. The reaction mixture was cooled down to room temperature, diluted with ethyl acetate, and washed with brine. The organic layer was dried over anhydrous sodium sulfate, and the resultant residue obtained after concentration under reduced pressure was purified by silica gel column chromatography (hexane:ethyl acetate=5:1, hexane:ethy acetate:chloroform=20:20:1, followed by chloroform:ethyl acetate=10:1), to give 9.23 g of 2,4-dichloro-6-(3,4-dimethoxy)phenylpyrimidine as yellow powder (yield 45%).
(Melting point: 165-167° C.)

(2) Synthesis of 2-chloro-4-(3,4-dimethoxy)phenyl-6-(pyrrolidin-1-yl)pyrimidine

The above obtained 2,4-dichloro-6-(3,4dimethoxy)phenyl-pyrimidine (3.00 g) and triethylamine (2.93 mL) were added to N,N-dimethylformamide (42 mL), and to the mixture was added pyrrolidine (966 µL) under ice cooling. The mixture was stirred at room temperature for 2 hours, and then, ice-cold water was added to the reaction mixture, and the mixture was extracted with ethyl acetate. The organic layer was washed with water and brine, dried over anhydrous sodium sulfate, and concentrated under reduced pressure. The residue was purified by silica gel column chromatography (hexane:ethylacetate=1:1), to give 3.10 g of 2-chloro-4-(3,4-dimethoxy)phenyl-6-(pyrrolidin-1-yl)pyrimidine as colorless crystals (yield 92%)
(Melting point: 133-135° C.)

(3) Synthesis of 4-(3,4-dimethoxy)phenyl-6-(pyrrolidin-1-yl)-2-[(E)-2-(tributylstannyl)ethenyl]pyrimidine According to the method described in literature of Stille et al. (Organic Synthesis, 1988, vol. 67, pp. 86-97), (E)-1,2-bis-(tributylstannyl)ethylene was obtained. This (E)-1,2-bis-(tributylstannyl)ethylene (11.71 g), 2-chloro-4-(3,4-dimethoxy)phenyl-6-(pyrrolidin-1-yl)pyrimidine (3.09 g) obtained in the above (2), dichlorobis(triphenylphosphine)-palladium(II) (343 mg), triphenylphosphine (507 mg), and copper (I) bromide (277 mg) were mixed in toluene (60 mL), and the mixture was refluxed under heating for 2 hours. The reaction mixture was cooled down to room temperature, and purified by silica gel column chromatography (hexane:ethyl acetate=10:1 to 5:1), to give 2.48 g of 4-(3,4-dimethoxy)phenyl-6-(pyrrollidin-1-yl)-2-[(E)-2-(tributylstannyl)ethenyl]pyrimidine as pale yellow oil (yield 43%).
IR (Neat): 1597, 1575, 1518; APCI-MS m/z 598 (M+H)$^+$]

(4) Synthesis of 2-chloro-4-(1-imidazolyl)quinazoline

To a suspension of 60% sodium hydride (426 mg) in tetrahydrofuran (4 mL)-N,N-dimethylformamide (24 mL) was added imidazole (725 mg), and the mixture was stirred at room temperature for 30 minutes. To the mixture was added dropwise a tetrahydrofuran solution (35 mL) of 2,4-dichloroquinazoline (2.12 g) synthesized according to the method of H. C. Scarborough et al. (Journal of Organic Chemistry, 1962, pp. 957-961), in ice-acetone bath, and the mixture was stirred for 30 minutes. The reaction mixture was poured into ice-cold water, and precipitated powder was collected by filtration, washed with water and dried. The obtained powder was purified by silica gel column chromatography, (ethyl acetate), to give 1.88 g of 2-chloro-4-(1-imidazolyl)-quinazoline as colorless crystals (yield 77%).
(Melting point: 168-170° C. (decomposition))

(5) Synthesis of 2-{(E)-2-[4-(1-imidazolyl)quinazolin-2-yl]}-ethenyl-4-(3,4-dimethoxy)phenyl-6-(pyrrolidin-1-yl)-pyrimidine A mixture of 2-chloro-4-(1-imidazolyl)quinazoline (1.44 g) obtained in the above (4), 4-(3,4-dimethoxy)phenyl-6-(1-pyrrolidinyl)-2-[(E)-2-(tributylstannyl)ethenyl]pyrimidine (2.47 g) obtained in the above (3), dichlorobis(triphenylphosphine)palladium(II) (144 mg), triphenylphosphine (216 mg), and copper (I) bromide (118 mg) in toluene (35 mL) was refluxed under heating for 2.5 hours. The reaction mixture was cooled down to room temperature, diluted with chloroform (10 mL), and purified by NH-silica gel column chromatography (hexane:chloroform=7:3, and then, 1:1) and subsequently by silica gel column chromatography (chloroform:methanol=50:1). The obtained powder was recrystallized from dichloromethane-ethyl acetate, to give 1.13 g of 2-{(E)-2-[4-(1-imidazolyl)quinazolin-2-yl]}ethenyl-4-(3,4-dimethoxy)phenyl-6-(pyrrolidin-1-yl)pyrimidine (free form) (Compound A) as yellow crystals (yield 54%).

(Melting point: 234-239° C.)

The invention claimed is:

1. A method for enhancing dopamine signals in the brain, which comprises administering to a patient in need thereof an effective amount of a compound having a phosphodiesterase 10 inhibitory activity together with inducing dopamine signals by L-dopa administration or by administration of a dopamine receptor agonist, and thereby enhancing dopamine signals in the brain of said patient; wherein the compound having phosphodiesterase 10 inhibitory activity is

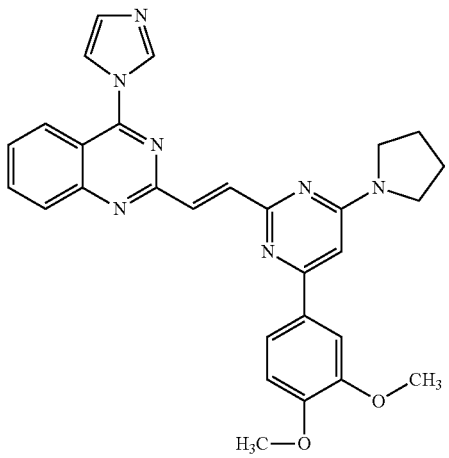

or a pharmaceutically acceptable salt thereof.

2. The method according to claim 1, wherein said patient is a patient afflicted with Parkinson's disease.

3. The method according to claim 1 or 2, wherein the dopamine signals are enhanced in a part of the brain, selected from the group consisting of corpus striatum, nucleus accumbens, olfactory tubercle and frontal lobe.

4. The method according to claim 1 or 2, wherein the dopamine signals are enhanced in the corpus striatum.

5. The method according to claim 1 or 2, wherein the dopamine signals are those induced by L-dopa administration.

6. The method according to claim 1 or 2, wherein the dopamine signals are those induced by administration of a dopamine receptor agonist.

7. The method according to claim 1 or 2, wherein the dopamine signals are those induced by administration of a dopamine type 2 receptor agonist.

8. The method according to claim 1 or 2, wherein the dopamine signals are those induced by administration of a dopamine type 2 receptor selective agonist.

9. The method according to claim 1 or 2, wherein the dopamine signals are those induced by administration of bromocriptine.

* * * * *